US012400327B2

(12) United States Patent
Sadri et al.

(10) Patent No.: US 12,400,327 B2
(45) Date of Patent: Aug. 26, 2025

(54) HYBRID CONVOLUTIONAL WAVELET NETWORKS FOR PREDICTING TREATMENT RESPONSE VIA RADIOLOGICAL IMAGES OF BOWEL DISEASE

(71) Applicant: Case Western Reserve University, Cleveland, OH (US)

(72) Inventors: Amir Reza Sadri, Cleveland Heights, OH (US); Satish E. Viswanath, Beachwood, OH (US); Thomas Desilvio, Lyndhurst, OH (US)

(73) Assignee: Case Western Reserve University, Cleveland, OH (US)

( * ) Notice: Subject to any disclaimer, the term of this patent is extended or adjusted under 35 U.S.C. 154(b) by 384 days.

(21) Appl. No.: 18/169,935

(22) Filed: Feb. 16, 2023

(65) Prior Publication Data

US 2023/0267607 A1    Aug. 24, 2023

Related U.S. Application Data

(60) Provisional application No. 63/311,468, filed on Feb. 18, 2022.

(51) Int. Cl.
*G06T 7/00* (2017.01)
*G16H 30/40* (2018.01)
*G16H 50/30* (2018.01)

(52) U.S. Cl.
CPC .......... *G06T 7/0012* (2013.01); *G16H 30/40* (2018.01); *G16H 50/30* (2018.01);
(Continued)

(58) Field of Classification Search
CPC ......... G06T 7/0012; G06T 2207/10081; G06T 2207/10088; G06T 2207/10116;
(Continued)

(56) References Cited

U.S. PATENT DOCUMENTS

| 11,120,312 B2 * | 9/2021 | Buckler | .................. G06F 18/29 |
| 2020/0380673 A1 * | 12/2020 | Wang | .................... G06T 7/0012 |

OTHER PUBLICATIONS

Fujieda, Shin, Kohei Takayama, and Toshiya Hachisuka. "Wavelet convolutional neural networks." arXiv preprint arXiv:1805.08620 (Year: 2018).*

(Continued)

*Primary Examiner* — Scott A Rogers
(74) *Attorney, Agent, or Firm* — Eschweiler & Potashnik, LLC

(57) ABSTRACT

In some embodiments, the present disclosure relates to a non-transitory computer-readable medium storing computer-executable instructions that, when executed, cause a processor to perform operations, including forming an imaging dataset having imaging data corresponding to one or more radiological images of a patient having a bowel disease; operating upon the imaging data with one or more convolutional neural network (CNN) segments configured to generate a plurality of CNN outputs, the one or more CNN segments respectively including a convolution layer configured to perform a convolution on the imaging data; and applying a wavelet network to the plurality of CNN outputs to generate a plurality of convolution wavelet network (CWN) outputs, the wavelet network being configured to decompose the plurality of CNN outputs according to a mother wavelet. A predictive signature associated with disease response or risk is constructed using the plurality of CWN outputs.

20 Claims, 14 Drawing Sheets

(52) U.S. Cl.
CPC ............... *G06T 2207/10072* (2013.01); *G06T 2207/10116* (2013.01); *G06T 2207/20064* (2013.01); *G06T 2207/20084* (2013.01); *G06T 2207/30028* (2013.01); *G06T 2207/30096* (2013.01)

(58) Field of Classification Search
CPC ........... G06T 2207/20064; G06T 2207/20084; G06T 2207/30028; G06T 2207/30096; G06H 30/20; G06H 30/40; G16H 50/20; G16H 50/30; A61B 5/4255; A61B 5/7275; A61B 5/7264–7267
See application file for complete search history.

(56) References Cited

OTHER PUBLICATIONS

Khatami, Amin, et al. "Convolutional neural network for medical image classification using wavelet features." 2020 international joint conference on neural networks (IJCNN). IEEE, (Year: 2020).*
Sadri, Amir Reza, et al. "Residual wavelon convolutional networks for characterization of disease response on MRI." International Conference on Medical Image Computing and Computer-Assisted Intervention. Cham: Springer Nature Switzerland, pp. 366-375 (Year: 2022).*
Yamashita, Rikiya, et al. "Convolutional neural networks: an overview and application in radiology." Insights into imaging 9, pp. 611-629 (Year: 2018).*

* cited by examiner

1000

| Approach | Parameters | Runtime | Accuracy | |
|---|---|---|---|---|
| | | | Training | Validation |
| CNN | 216830 | 98.23 | 69.04 | 71.56 |
| DWN-MLP | 4637834 | 398.37 | 64.83 | 76.33 |
| DHCWN | 220646 | 112.59 | 90.67* | 91.17* |

1200

| | Approach | Parameters | Runtime (min) | Accuracy | | AUC | |
|---|---|---|---|---|---|---|---|
| | | | | Discovery | Validation | Discovery | Validation |
| 1202 → | CNN | 216830 | 98.23 | 69.12 ± 0.24 | 71.56 | 0.60 ± 0.11 | 0.56 |
| 1204 → | DWN-MLP (Mexican hat) | 4637834 | 395.82 | 64.74 ± 0.15 | 75.18 | 0.61 ± 0.12 | 0.60 |
| 1206 → | DWN-MLP (Morlet) | 4637834 | 398.37 | 70.83 ± 0.11 | 76.34 | 0.64 ± 0.04 | 0.63 |
| 1208 → | DHCWN (Mexican hat) | 229646 | 110.61 | 87.67 ± 0.08 | 87.73 | 0.73 ± 0.07 | 0.72 |
| 1210 → | DHCWN (Morlet) | 229646 | 112.59 | 88.78 ± 0.05* | 89.45 | 0.77 ± 0.02* | 0.74 |

| | Approach | Parameters | Runtime (min) | Accuracy | | AUC | |
|---|---|---|---|---|---|---|---|
| | | | | Discovery | Validation | Discovery | Validation |
| 1214 → | CNN | 336067 | 157.17 | 71.08 ± 0.14 | 72.73 | 0.62 ± 0.19 | 0.59 |
| 1216 → | DWN-MLP (Mexican hat) | 788432 | 692.69 | 68.21 ± 0.11 | 67.33 | 0.64 ± 0.10 | 0.61 |
| 1218 → | DWN-MLP (Morlet) | 788432 | 701.84 | 69.79 ± 0.08 | 70.86 | 0.65 ± 0.04 | 0.64 |
| 1220 → | DHCWN (Mexican hat) | 417020 | 209.06 | 90.32 ± 0.07 | 90.87 | 0.74 ± 0.05 | 0.73 |
| 1222 → | DHCWN (Morlet) | 417020 | 212.70 | 90.55 ± 0.03* | 91.23 | 0.79 ± 0.06* | 0.76 |

| Approach | Parameters | C1 (Rectal Cancer, pre-CRT) Accuracy | | C2 (Rectal Cancer, post-CRT) Accuracy | | C3 (Crohn's Disease) Accuracy | |
|---|---|---|---|---|---|---|---|
| | | Discovery | Validation | Discovery | Validation | Discovery | Validation |
| 1402 → BWCS-VGG-4 ($v_p = 0$) | 842,562 | 0.75 ± 0.15 | 0.72 | 0.76 ± 0.12 | 0.75 | 0.71 ± 0.12 | 0.71 |
| 1404 → BWCS-VGG-8 ($v_p = 1$) | 781,388 | 0.86 ± 0.08 | 0.78 | 0.86 ± 0.06 | 0.80 | 0.86 ± 0.08 | 0.81 |
| 1406 → BWCS-ResNet-18 ($v_p = 0$) | 967,833 | 0.75 ± 0.06 | 0.72 | 0.77 ± 0.06 | 0.77 | 0.74 ± 0.07 | 0.73 |
| 1408 → BWCS-ResNet-18 ($v_p = 1$) | 1,848,988 | 0.94 ± 0.03* | 0.83 | 0.95 ± 0.03* | 0.85 | 0.92 ± 0.03* | 0.88 |
| 1410 → VGG-16 | 138,357,544 | 0.86 ± 0.06 | 0.75 | 0.87 ± 0.06 | 0.79 | 0.85 ± 0.06 | 0.83 |
| 1412 → VGG-19 | 143,667,240 | 0.87 ± 0.06 | 0.75 | 0.86 ± 0.04 | 0.80 | 0.86 ± 0.07 | 0.84 |
| 1414 → ResNet-18 | 11,178,680 | 0.84 ± 0.06 | 0.75 | 0.86 ± 0.03 | 0.81 | 0.87 ± 0.05 | 0.85 |
| 1416 → ResNet-50 | 23,512,130 | 0.86 ± 0.06 | 0.78 | 0.91 ± 0.04 | 0.81 | 0.89 ± 0.04 | 0.86 |

HYBRID CONVOLUTIONAL WAVELET NETWORKS FOR PREDICTING TREATMENT RESPONSE VIA RADIOLOGICAL IMAGES OF BOWEL DISEASE

REFERENCE TO RELATED APPLICATION

This application claims the benefit of U.S. Provisional Application No. 63/311,468, filed on Feb. 18, 2022, the contents of which are hereby incorporated by reference in their entirety.

FEDERAL FUNDING NOTICE

This invention was made with government support under CA248226 awarded by the National Institutes of Health and W81XWH-21-1-0345 awarded by the Department of Defense. The government has certain rights in the invention.

BACKGROUND

Deep learning is a type of machine learning that works with artificial neural networks, which are designed to imitate how humans think and learn. In recent years, deep learning technology has found applications in many fields, including medical imaging.

BRIEF DESCRIPTION OF THE DRAWINGS

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

FIGS. 12A-12B illustrate tables showing example performance parameters of disclosed DHCWNs having different Mother wavelets in comparison to different machine learning models operated to distinguish a pCR from a non-pCR.

FIG. 14 illustrates a table showing exemplary performance parameters for disclosed RWCNs in comparison to different machine learning models architectures in distinguishing pCR from non-pCR for different diseases.

DETAILED DESCRIPTION

Figure 1:
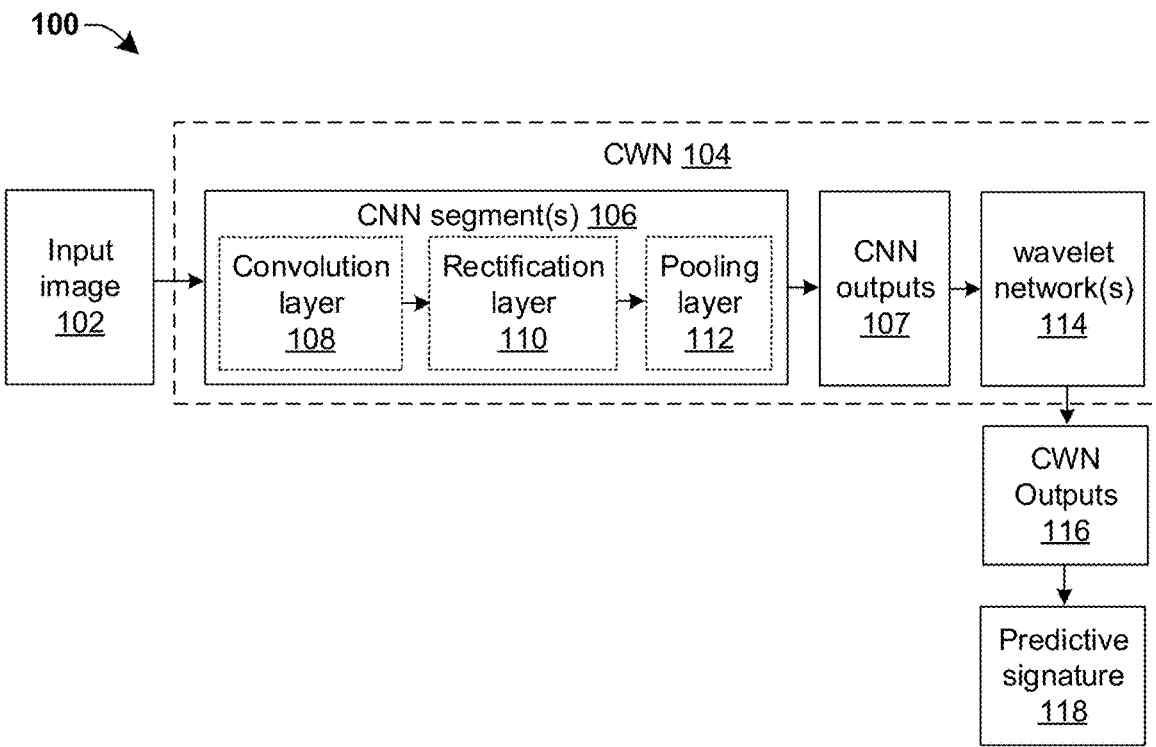
FIG. 1 illustrates a block diagram showing some embodiments of a convolutional wavelet network (CWN) comprising one or more wavelet networks (WNs) integrated within a convolutional neural network (CNN) architecture.

The description herein is made with reference to the drawings, wherein like reference numerals are generally utilized to refer to like elements throughout, and wherein the various structures are not necessarily drawn to scale. In the following description, for purposes of explanation, numerous specific details are set forth in order to facilitate understanding. It may be evident, however, to one of ordinary skill in the art, that one or more aspects described herein may be practiced with a lesser degree of these specific details. In other instances, known structures and devices are shown in block diagram form to facilitate understanding.

Convolutional neural networks (CNNs) are a type of machine learning classifier that is commonly used in the analysis of images and/or audio signals. CNNs may be configured to receive an input image, assign importance (e.g., via learnable weights) to different features in the input image, and use the learnable weights to differentiate the different features from one another.

The basic architecture of a CNN comprises three different layers: a convolution layer, a pooling layer, and a fully connected layer. The convolution layer is configured to receive an input image and to perform a convolution on the input image to generate convolved data. The pooling layer is configured to down-sample the convolved data to form a feature map, which may identify features (e.g., edges, corners, etc.) within the input image. The fully connected layer uses an activation function to map the feature map into final outputs that can be used to classify the input image.

In recent years, CNNs have found increased use within medical applications. For example, CNNs may be used to identify features within medical images of a patient (e.g., radiological images, digitized images, etc.), and to subsequently use the features to make a prognosis relating to the patient. While the use of CNNs has been moderately successful in analyzing medical images, there are still many medical applications (e.g., rectal cancer, Crohn's disease, etc.) in which CNNs have failed to accurately diagnose patients. This may be because activation functions used by CNNs to generate final outputs are fixed (e.g., monotonic) functions that may be unstable to due to infinite energy levels (e.g., in a ReLU function of a ResNET model).

Wavelets are wave-like oscillations that can be varied in scale and time. A wavelet transform is a projection of a signal into a set of wavelets (e.g., de-composing a signal into shifted and scaled versions of a mother wavelet). For example, during a wavelet transform a function can be approximated by adding different versions of a method wavelet having varying scales and time shifts. It has been appreciated that the use of wavelets as an activation function of a CNN architecture may lead to improved characterization of a medical image, thereby improving an ability of health care professionals to capture subtle patterns within the medical image.

The present disclosure relates to a convolutional wavelet network (CWN) that utilizes both deep learning (e.g., convolutional neural networks) and wavelet networks to generate a predictive signature from a digitized image of a patient. In some embodiments, the disclosed CWN comprises one or more CNN segments configured to operate upon an input image of a patient having a bowel disease (e.g., rectal cancer, Crohn's disease, etc.) to generate a plurality of CNN outputs. The plurality of CNN outputs are provided as inputs to a wavelet network. The wavelet network is configured to perform a wavelet decomposition on the plurality of CNN outputs to generate a plurality of CWN outputs that can be used to construct a predictive signature of the bowel disease for the patient. Unlike the fixed and/or monotonic activation functions that are commonly used in convolutional neural networks (CNNs), the disclosed CWN uses a wavelet network to operate as a flexible activation function. Therefore, the disclosed CWN may be able to capture more complex structures from medical images and thereby aid health care professionals in identifying features that have a high correlation to a prognosis (e.g., a pathologic complete response (pCR) of a patient). For example, the disclosed CWN may exploit subtle differences in oriented and scaled textures that may allow differentiation between tumors (e.g., lesions) which do or do not respond to chemoradiation.

FIG. 1 illustrates a block diagram showing some embodiments of an image analysis system 100 comprising a convolutional wavelet network (CWN) having one or more wavelet networks (WNs) integrated within a convolutional neural network (CNN) architecture.

The image analysis system 100 comprises a CWN 104 configured to receive an input image 102. The input image 102 comprises a plurality of pixels or voxels respectively having an associated intensity. In some embodiments, the input image 102 may comprise a radiological image (e.g., a magnetic resonance image (MRI), a computed tomography (CT) image, magnetic resonance elastography (MRE), or the like) of a patient having a disease (e.g., a bowel disease such a rectal cancer, Crohn's disease, or the like).

The CWN 104 comprises one or more convolutional neural network (CNN) segments 106 (e.g., sequence blocks) and one or more wavelet networks (WNs) 114. The one or more CNN segments 106 are configured to operate upon the input image 102 to generate a plurality of CNN outputs 107.

The plurality of CNN outputs 107 may correspond to one or more features (e.g., texture patterns, shapes, edges, or the like) of the input image 102. The one or more CNN segments 106 may respectively comprise one or more convolution layers 108 configured to perform a convolution upon the input image 102 to generate a feature map. The feature map may be subsequently acted on by a rectification layer 110 (e.g., configured to apply a nonlinear activation function, such as rectified linear activation function (ReLU), exponential linear unit (ELU), Leaky ReLU variants, or the like) and/or a pooling layer 112 to generate the plurality of CNN outputs 107.

The plurality of CNN outputs 107 are provided from one of the one or more CNN segments 106 to the one or more WNs 114. The one or more WNs 114 may be disposed downstream of the one or more CNN segments 106, so as to act as a final activation layer within the CWN 104. The one or more wavelet networks 114 are configured to decompose the one or more CNN outputs 107 according to a mother wavelet into a plurality of wavelons. The plurality of wavelons are fully connected to generate one or more CWN outputs 116. In some embodiments, the one or more CNN outputs 107 may be expanded according to the function $f(x) = \Sigma_{i \in \mathbb{Z}} \Psi_i(x)$ where $w_i$ are decomposition coefficients (e.g., weight, scale, shift, bias, etc.) and $w_i \Psi_i(x)$ is a mother wavelet. For example, the one or more wavelet networks 108 may be configured to expand the one or more CNN outputs 107 according to shifted and/or scaled versions of the mother wavelet. In some embodiment, the one or more wavelet networks 114 may respectively comprise a three-layer network comprising an input layer, a hidden layer, and an output layer. The input layer comprises variables corresponding to the one or more CNN outputs 107. The hidden layer comprises a plurality of wavelons (e.g., wavelet neurons), which respectively comprise different versions of a mother wavelet (e.g., shifted and/or scaled versions of a mother wavelet). The output layer comprises CWN outputs 116 that may be used to classify the input image 102.

In some embodiments, the plurality of CWN outputs 116 may be used to generate a predictive signature 118 relating to the disease of the patient. In some embodiments, the predictive signature may relate a response of the disease to treatment (e.g., distinguishing a pCR from a non-pCR), thereby indicating whether the patient may need a treatment plan including pharmaceutical therapy or surgery. In other embodiments, the predictive signature may relate a risk of the disease (e.g., a risk of recurrence after treatment, an overall survival of the patient, etc.).

Because the one or more wavelet networks 114 utilize a mother wavelet that is a variable (e.g., non-monotonic) function, the CWN 104 may be able to capture more complicated patterns within the input image 102 (e.g., in comparison to a CNN comprising a fixed activation function). The ability to capture more complicated patterns within the input image 102 may allow for the disclosed CWN 104 to more accurately identify features that may be used to generate the predictive signature 118 and to thus more accurately indicate a prognosis of a patient. For example, in evaluating pre-treatment rectal cancer MRI scans to predict a pathologic complete response (pCR) of a patient to neoadjuvant chemoradiation, the disclosed CWN 104 yielded a predictive signature with significantly better performance compared to a typical convolutional neural network (CNN) and/or a multilayer wavelet perceptron (DWN-MLP).

Figure 2:
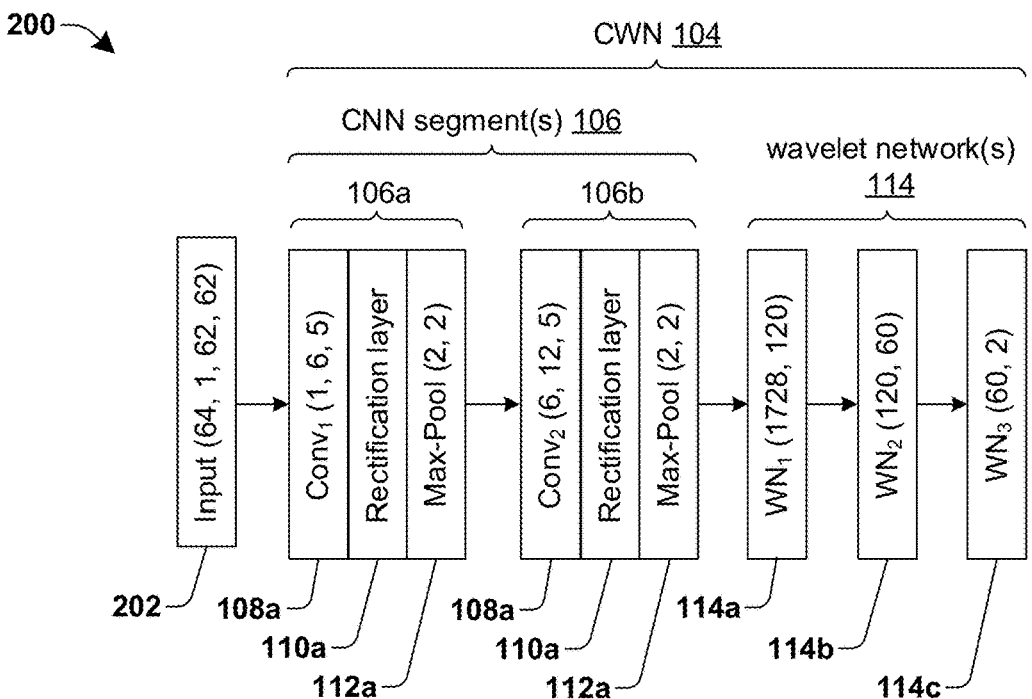
FIG. 2 illustrates a block diagram showing some additional embodiments of a CWN comprising one or more WNs integrated within a CNN architecture.

FIG. 2 illustrates a block diagram showing some additional embodiments of an image analysis system 200 comprising a CWN having one or more wavelet networks integrated within a CNN architecture.

The image analysis system 200 comprises a CWN 104 having one or more CNN segments 106 configured to receive an input image 102 comprising a plurality of pixels or voxels. In some embodiments, the input image 102 may comprise a radiological image of a patient. In some embodiments, the patient may have a bowel disease (e.g., colorectal cancer, rectal cancer, Crohn's disease, or the like). In some embodiments, the input image 102 may comprise a radiological image having a region of interest including one or more lesions (e.g., tumors). The input image 102 may have an image size that is 50 pixels×50 pixels, 62 pixels×62 pixels, or other similar values.

The one or more CNN segments 106 comprise a first CNN segment 106a and a second CNN segment 106b downstream of the first CNN segment 106a. The first CNN segment 106a comprises a first convolution layer 108a configured to perform a convolution, a first rectification layer 110a configured to perform a rectification function (e.g., a RELU function) on an output of the first convolution layer 108a, and a first pooling layer 112a configured to down sample the output of the first rectification layer 110a. The second CNN segment 106b comprises a second convolution layer 108b configured to perform a convolution, a second rectification layer 110b configured to perform a ReLU rectification function on an output of the second convolution layer 108b, and a second pooling layer 112b configured to down sample the output of the second rectification layer 110b. One or more CNN outputs are output from a last one of the one or more CNN segments 106.

In some embodiments, convolution layers 108a-108b may be configured to perform a convolution by acting upon an input matrix with a kernel. In such embodiments, the kernel is operated to slide along the input matrix to generate a feature map. In some embodiments, the first convolution layer 108a may have a kernel size of 5 (e.g., a 5×5 matrix) and a stride length of 1. In some embodiments, the first pooling layer 112a may have a kernel size of 2 (e.g., a 2×2 matrix), a stride of length 2, a padding of 0, and a dilation of 1. In some embodiments, the second convolution layer 108b may have a kernel size of 5 and a stride length of 1. In some embodiments, the second pooling layer 112b may have a kernel size of 2 (e.g., a 2×2 matrix), a stride of length 2, a padding of 0, and a dilation of 1.

The one or more CNN outputs are provided to one or more WNs 114 disposed downstream of the one or more CNN segments 106. The one or more WNs 114 may respectively comprise an input layer, one or more hidden layers, and an output layer. The one or more hidden layers respectively comprise wavelet neurons (wavelons), which include shifted and scaled versions of a mother wavelet. In some embodiments, the CWN 104 may comprise a residual wavelon convolutional network (RWCN) including one or more WNs 114 having skip connections extending between the input layer and the output layer. The skip connections are configured to enable residual learning. The residual learning enables the CWN to more efficiently capture high-dimensional disease response-specific patterns from medical images. In other embodiments, the CWN may comprise a deep hybrid convolutional wavelet network (DHCWN) including one or more WNs 114 without skip connections.

In some embodiments, the one or more WNs 114 respectively comprise wavelons that are subject to four different decomposition coefficients: a wavelon weight, a wavelon bias, a wavelon shift, and a wavelon scale. To decrease a complexity of calculations within the one or more WNs, the decomposition coefficients (e.g., weight, scale, shift, bias) may be defined in a tensor-based actions. For example, a tensor used within the one or more WNs may comprise different components respectively corresponding to a different decomposition coefficient. Using tensor-based actions reduces a time that it takes for the one or more WNs to operated (e.g., a time that it takes to apply a new activation function or pre-defined layer).

Typically, wavelet networks comprise three hidden layers. In some embodiments, the one or more WNs 114 may comprise four or more hidden layers. This is because function complexity dictates selection of a number of wavelons in a hidden layer (e.g., so that as problem complexity increases, a number of wavelons also increases). By increasing a number of hidden layers in the one or more WNs 114 to be greater than three, the number of wavelons in each hidden layer can be kept lower, thereby decreasing complexity of the one or more WNs 114. By decreasing a complexity of the one or more WNs 114, the one or more WNs 114 do not suffer from wavelet initialization and/or training complications that typically limit the applications of wavelet networks to low dimensional problems.

In some embodiments, the one or more WNs 114 may comprise a first WN 114a, a second WN 114b, and a third WN 114c sequentially coupled to one another. An input layer of the first WN 114a comprises variables corresponding to the one or more CNN outputs. An output layer of the third WN 114c comprises CWN outputs, which may be used to classify the input image 102. By sequentially coupling the one or more WNs 114 together, the one or more WNs 114 are able to approximate the CWN outputs through gradient descent.

In some embodiments, the first WN 114a, the second WN 114b, and the third WN 114c may comprise wavelons that utilize mother wavelets comprising an m-dimensional Mexican hat radial mother wavelet $$\left(\text{e.g., } \psi(x) = (1-x^2)\exp\left(-\frac{x^2}{2}\right)\right).$$

In other embodiments, the first WN 114a, the second WN 114b, and the third WN 114c may comprise wavelons that utilize mother wavelets comprising orthogonal wavelets (e.g., a Coiflet), a wavelet frame (e.g., a Morlet function, etc.), or the like. In some embodiments, each of the one or more WNs 114 may output less outputs than a preceding WN. For example, the first WN 114a may comprise a wavelon shape of 1024×512 (e.g., 1024 inputs and 512 outputs), the second WN 114b may comprise a wavelon shape of 12×256, and the third WN 114c may comprise a wavelon shape of 256×128.

It will be appreciated that the disclosed methods and/or block diagrams may be implemented as computer-executable instructions, in some embodiments. Thus, in one example, a computer-readable storage device (e.g., a non-transitory computer-readable medium) may store computer executable instructions that if executed by a machine (e.g., computer, processor) cause the machine to perform the disclosed methods and/or block diagrams. While executable instructions associated with the disclosed methods and/or block diagrams are described as being stored on a computer-readable storage device, it is to be appreciated that executable instructions associated with other example disclosed methods and/or block diagrams described or claimed herein may also be stored on a computer-readable storage device.

Figure 3A:
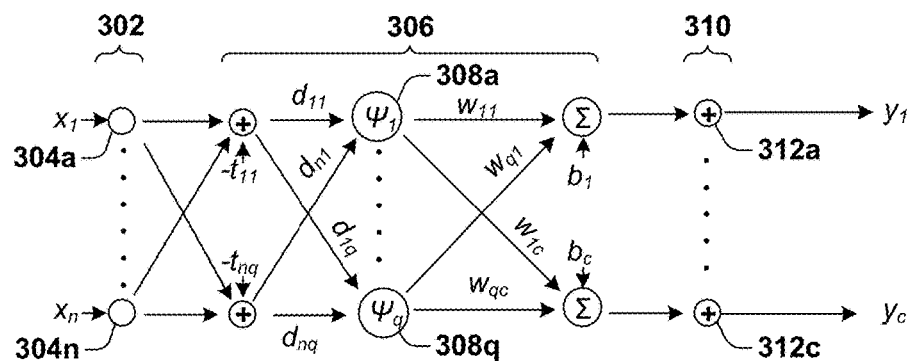
FIGS. 3A-3B illustrate block diagrams showing some embodiments of a disclosed WN.
Figure 3B:
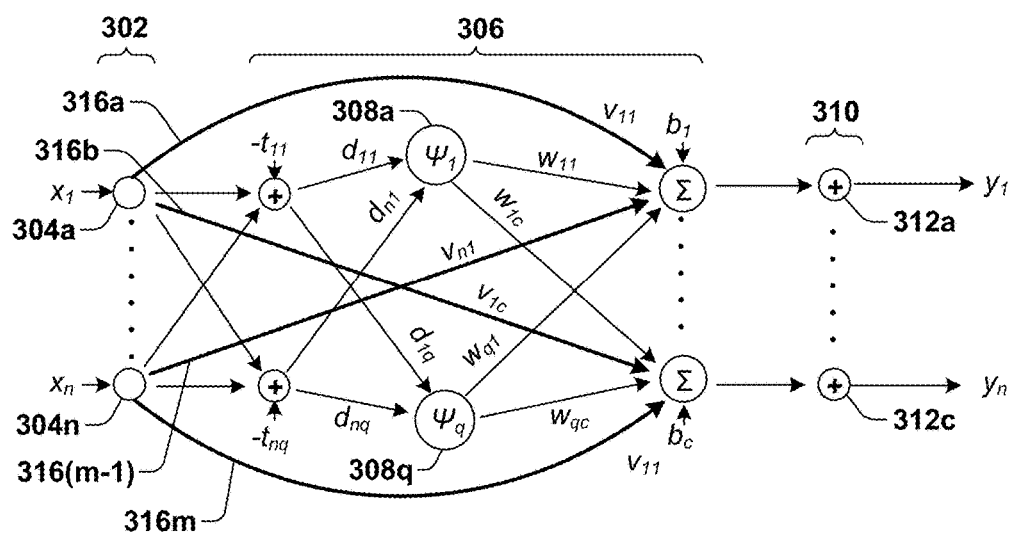

FIGS. 3A-3B illustrate block diagrams showing some embodiments of a disclosed wavelet network.

FIG. 3A illustrates some embodiments of a wavelet network 300 comprising a three-layer network comprising an input layer 302, a hidden layer 306, and an output layer 310.

The input layer 302 comprises a plurality of inputs 304a-304n. In some embodiments, the plurality of inputs 304a-304n may comprise n inputs received from an upstream CNN segment. The hidden layer 306 comprises a plurality of wavelons 308a-308q (e.g., wavelet neurons). The plurality of wavelons 308a-308q utilize a mother wavelet $\Psi_q$ having different shift parameters and different scale parameters. In some embodiments, the mother wavelet $\Psi_q$ may comprise an m-dimensional Mexican hat $$\left(\text{e.g., } \psi(x) = (1-x^2)\exp\left(-\frac{x^2}{2}\right)\right),$$

a Morlet wavelet $$\left(\text{e.g., } \psi(x) = \exp\left(-\frac{x^2}{2}\right)\cos(5x)\right),$$

or the like.

The plurality of inputs 304a-304n are selectively shifted according to wavelet shift parameters ($t_{ij}$) and wavelet scale parameters ($c_{ij}$) to form the plurality of wavelons 308a-308q respectively comprising a different version of a mother wavelet $\Psi_q$ (e.g., a wavelon is a version of a mother wavelet with a different shift and/or scaling than other wavelons). The wavelet shift parameters ($t_{ij}$) are configured to shift a position (e.g., in time) of the mother wavelet $\Psi_q$. The wavelet scale parameters ($d_{ij}$) are configured to change a size (e.g., amplitude) of the mother wavelet $\Psi_q$.

The output layer 310 is a fully connected layer having a plurality of CWN outputs 312a-312c. In some embodiments, the plurality of CWN outputs 312a-312c may comprise c outputs. The plurality of CWN outputs 312a-312c are respectively a function of a sum of the plurality of wavelons 308a-308q weighted with different wavelon weight parameters ($w_{ij}$). For example, CWN output 312a is a function of a sum of a first wavelon 308a weighted according to weight parameter $w_{11}$ and a $q^{th}$ wavelon 308q weighted according to weight parameter $w_{q1}$ and CWN output 312c is a function of a sum of the first wavelon 308a weighted according to weight parameter $w_{1c}$ and the $q^{th}$ wavelon 308q weighted according to weight parameter $w_{qc}$. In some embodiments, the plurality of CWN outputs 312a-312c are further functions of sums of a wavelon bias parameter ($b_p$). In such embodiments, the plurality of CWN outputs 312a-312c are a function of wavelon bias parameters ($b_p$) added to a sum of products of different wavelon weight parameters ($w_{ij}$) and the plurality of different versions of the mother wavelet.

In some embodiments, the plurality of outputs 312a-312c may be obtained according to the equation $y_p = \Sigma_{i=1}^{q} w_{ip} \Psi(D_i(x-t_i)+b_p$, for a wavelet network having n inputs ($x = [x_1, \ldots, x_n]^T$), q wavelons in the hidden layer 306, and c outputs. In such embodiments, $t_i$ are translation vectors, $D_i$ are diagonal dilation matrices specified by dilation vectors $d_i$ (e.g., $D_i$=diag ($d_i$), $d_i \in \mathbb{R}_+^n$)

By selecting an appropriate mother wavelet and considering a sample of input/output pairs, the wavelet network 300 has four different types of parameters (e.g., weight, bias, shift, and scale) which can be optimized during a learning process. Therefore, during operation of the disclosed CWN, the wavelet network 300 will operate to train the wavelet shift parameters ($t_{ij}$), the wavelet scale parameters ($d_{ij}$), the wavelon bias parameters ($b_p$), and/or the wavelon weight parameters ($d_{ij}$) to determine the plurality of CWN outputs 312a-312c in a manner that allows for classification of an input image.

FIG. 3B illustrates some additional embodiments of a wavelet network 314 comprising a three-layer network comprising an input layer 302, a hidden layer 306, and an output layer 310.

The input layer 302 comprises a plurality of inputs 304a-304n. The hidden layer 306 comprises a plurality of wavelons 308a-308q (e.g., wavelet neurons) configured to utilize a mother wavelet $\Psi_q$ having different shift parameters and weight parameters. The output layer 310 is a fully connected layer having c outputs 312a-312c.

In some embodiments, the wavelet network 314 may comprise a plurality of skip connections 316a-316m extending between the input layer 302 and the output layer 310. The plurality of skip connections 316a-316m may be weighted according to skip connection weight parameters factors ($v_{jk}$) (wherein i=1 to q and j=1 to n). A plurality of CWN outputs 312a-312c are a function of weighted versions of one or more of the plurality of skip connections 316a-316m. For example, CWN output 312a is a function of a sum of a first wavelon 308a weighted according to weight parameter $w_{11}$, a $q^{th}$ wavelon weighted according to weight parameter $w_{q1}$, a first skip connection 316a weighted according to skip connection weight parameter vii, and a second skip connection 316(m−1) weighted according to skip connection weight parameter $v_{nc}$. In some embodiments, the wavelon weight parameters may be set equal to the skip connection weight parameters (e.g., $w_{ij}=v_{ij}$), while in other embodiments the wavelon weight parameters may be different than the skip connection weight parameters.

The plurality of skip connections 316a-316m help preserve a gradient norm and lead to a stable back propagation via residual learning. Weighting the plurality of skip connections 316a-316m results in an uninterrupted gradient flow between the input layer 302 and the output layer 310, thus mitigating the vanishing gradient problem. Furthermore, the plurality of skip connections 316a-316m may allow for faster convergence by a disclosed CWN to a lower loss function, thereby allowing the CWN to have a faster and more accurate model convergence.

During operation, the wavelet network 314 will operate to train the wavelet shift parameters ($t_{ij}$), the wavelet scale parameters ($d_{ij}$), the a wavelon bias parameters ($b_p$), the wavelon weight parameters ($w_{ij}$), and/or the skip connection weight parameters ($v_{jk}$) to determine the plurality of CWN outputs 312a-312c in a manner that allows for classification of an input image.

Figure 4:
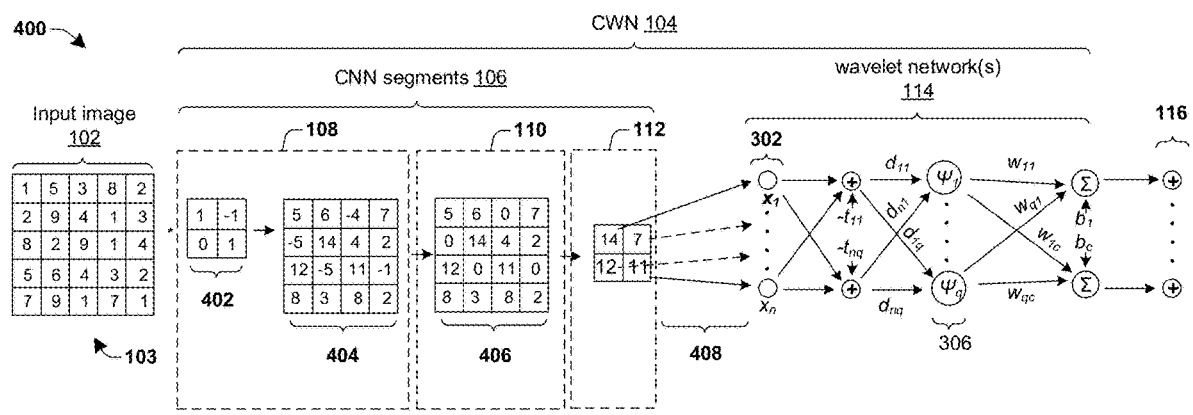
FIG. 4 illustrates a block diagram showing some additional embodiments of a CWN comprising one or more WNs integrated within a CNN architecture.

FIG. 4 illustrates a block diagram showing some exemplary embodiments of an image analysis system 400 comprising a disclosed CWN. It will be appreciated that the values within illustrated matrices of FIG. 4 are exemplary values that are merely intended to aid the reader in understanding.

The image analysis system 400 comprises a CWN 104 configured to receive an input image 102. The input image 102 is represented as an input matrix 103 comprising rows and columns having values that respectively correspond to a value of a pixel or voxel within the input image 102. The input matrix 103 is provided to one or more CNN segments 106. The one or more CNN segments 106 comprise a convolution layer 108 configured to act upon the input matrix 103 with a kernel 402 to generate a feature map 404. The kernel 402 is configured to perform a convolution on the input matrix 103 by sliding over the input matrix 103 at a stride rate. A rectification layer 110 is configured to apply a rectification function to the feature map 404 to generate a rectification map 406. In some embodiments, the rectification function may comprise a ReLU function (e.g., a piecewise linear function that will act upon the feature map 404 to that will output a value of the feature map directly if it is positive, or otherwise zero). A pooling layer 112 is configured to perform a pooling operation on the rectification map 406. The pooling operation down samples the rectification map 406 by summarizing a presence of features in regions of the rectification map 406.

The rectification map 406 is flattened 408 to generate CNN outputs, which are provided as inputs to an input layer 302 of one or more wavelet networks 114. The one or more wavelet networks 114 are configured to determine a set of wavelon weight parameters ($w_{ij}$), wavelet shift parameters ($s_{ij}$), wavelet scale parameters ($d_{ij}$), and/or wavelon bias parameters ($b_p$), and to generate a plurality of CWN outputs 116. The plurality of CWN outputs 116 are indicative of features within the input image 102. In some embodiments, from the plurality of CWN outputs 116, a predictive signature may be constructed to correspond to a prognosis. In some embodiments, the one or more wavelet networks 114 may further comprise skip connections (e.g., as shown in FIG. 3B).

Figure 5:
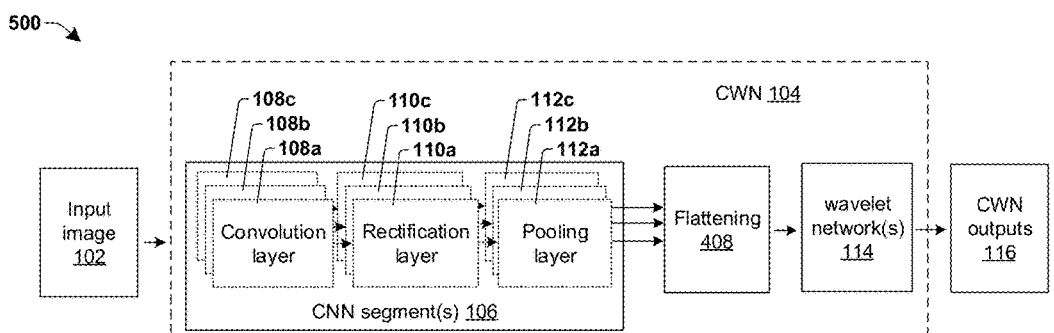
FIG. 5 illustrates a block diagram showing some additional embodiments of a CWN comprising one or more WNs integrated within a CNN architecture.

FIG. 5 illustrates a block diagram showing some additional embodiments of an image analysis system 500 comprising a disclosed CWN.

The image analysis system 500 comprises a CWN 104 configured to receive an input image 102 as an input matrix. The CWN 104 comprises one or more CNN segments 106 that respectively include a plurality of convolution layers 108a-108c configured to act upon the input matrix with different kernels to generate a plurality of feature maps (e.g., a first kernel is configured to operate upon the input matrix to generate a first feature map, a second kernel is configured to operate upon the input matrix to generate a second feature map, etc.). A plurality of rectification layers 110a-110c are configured to apply a rectification function (e.g., a ReLU function) to the plurality of feature maps to generate a plurality of rectification maps. A plurality of pooling layer 112a-112c are configured to perform a pooling operation on the plurality of rectification maps.

The outputs of the plurality of pooling layers 112a-112c are flattened 408 and then provided to inputs of an input layer of one or more wavelet networks 114. The one or more wavelet networks 114 are configured to determine wavelon weight parameters ($w_{ij}$), wavelet shift parameters ($s_{ij}$), wavelet scale parameters ($d_{ij}$), and/or wavelon bias parameters ($b_p$), and to generate a plurality of CWN outputs 116. The plurality of CWN outputs 116 are indicative of features within the input image 102. From the plurality of CWN outputs 116, the input image 102 can be classified to determine to a prognosis. In some embodiments, the one or more wavelet networks 114 may further comprise skip connections (e.g., as shown in FIG. 3B).

In some embodiments, the input image 102 comprises a plurality of channels that are represented by a plurality of input matrices respectively corresponding to a color. In some such embodiments, the plurality of different kernels may correspond to different colors (e.g., a first kernel may act upon a first input matrix to identify features having a first color (e.g., Red), a second kernel may act upon a second input matrix to identify features having a second color (e.g., Green), a third kernel may act upon a third input matrix to identify features having a third color (e.g., Blue), etc.), so that the plurality of different kernels form the plurality of different feature maps.

Figure 6A:
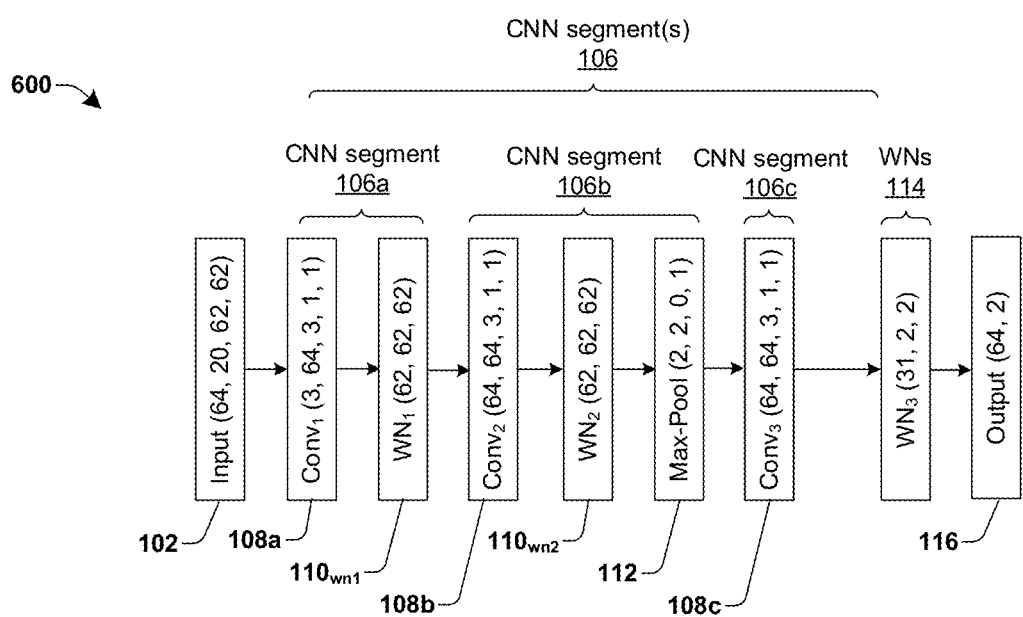
FIGS. 6A-6B illustrate block diagrams showing some additional embodiments of a CWN comprising one or more WNs integrated within a CNN architecture.
Figure 6B:
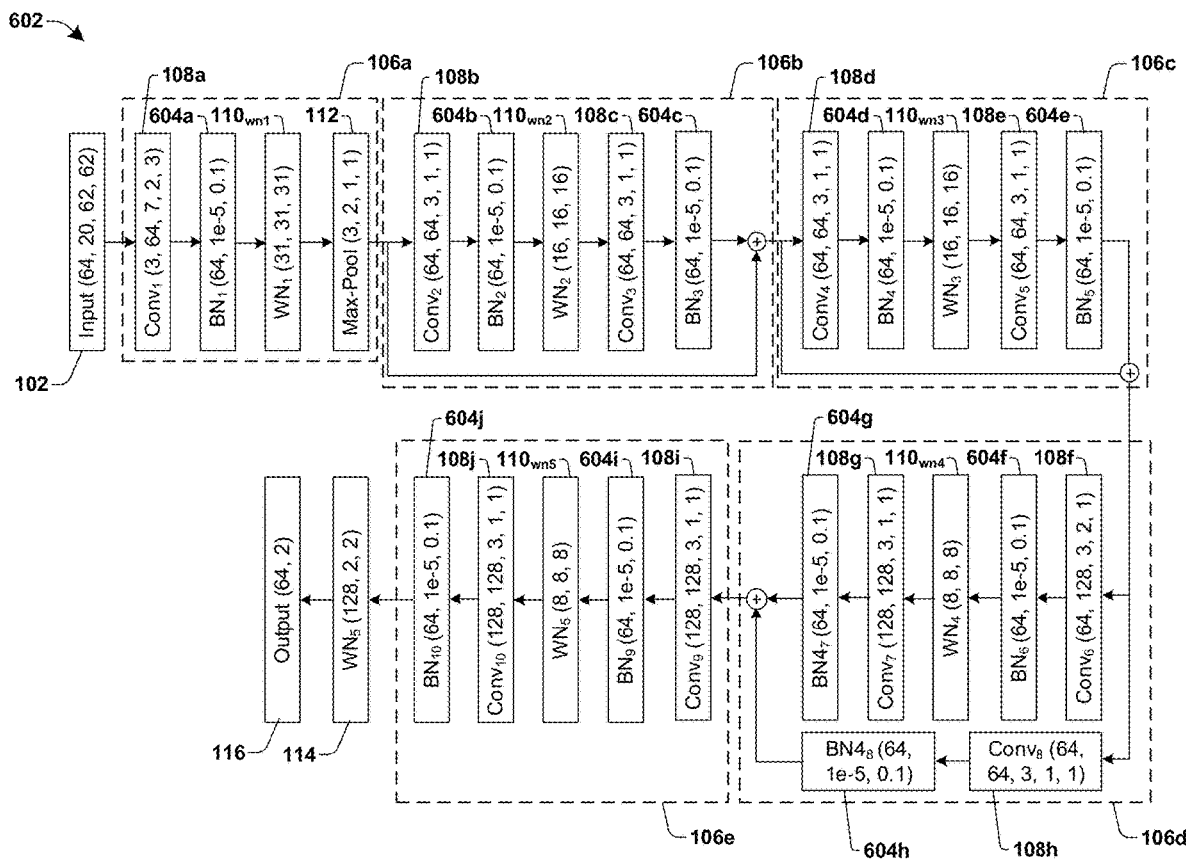

It will be appreciated that the disclosed CWN may have different architectures that will utilize different numbers of convolutional segments and/or wavelet networks. FIGS. 6A-6B illustrate block diagrams showing some additional embodiments of disclosed CWN architectures. It will be appreciated that the disclosed CWN architectures are not limiting but rather are only examples of CWN architectures that may fall within the disclosed CWN.

FIG. 6A illustrates a block diagram of a disclosed CWN 600 integrated within a RWCN-VGG-6 (residual wavelon convolutional network—visual geometry group) architecture.

The CWN 600 comprises a RWCN-VGG-6 architecture having three CNN segments 106a-106c and a WN 114 downstream of the three CNN segments 106a-106c. In total, the RWCN-VGG-6 architecture comprises 3 convolution blocks 108a-108c, 1 pooling layer 112, and 3 wavelet networks (WNs), including additional wavelet networks $110_{wn1}$-$110_{wn2}$ and wavelet network 114. Convolution layer 108a is configured to receive an input image 102 (e.g., as an input matrix) and to perform one or more first convolutions on the input image 102. The output of convolution layer 108a is flattened and provided to additional wavelet network $110_{wn1}$ as a first WN input. Additional wavelet network $110_{wn1}$ is configured to generate first WN outputs, which are provided as inputs to convolution layer 108b. Convolution layer 108b is configured to perform one or more second convolutions on the first WN outputs. The output of convolution layer 108b is flattened and provided to additional wavelet network $110_{wn2}$ as a second WN input. Additional wavelet network $110_{wn2}$ is configured to generate second WN outputs, which are provided as inputs to a pooling layer 112 configured to perform a max pooling operation on the second WN outputs to generate a pooled layer. Convolution layer 108c is configured to receive the pooled layer and to perform one or more third convolutions on the pooled layer. The output of convolution layer 108c is flattened and provided to wavelet network 114 as a third WN input. The wavelet network 114 is configured to generate CWN outputs.

In some embodiments, each of the additional wavelet networks $110_{wn1}$-$110_{wn2}$ and wavelet network 114 may comprise internal skip connections (e.g., as shown in FIG. 3B) to enable residual learning. Furthermore, by building the additional wavelet networks $110_{wn1}$-$110_{wn2}$ to have skip connections, later layers can learn lesser semantic information derived from initial input layers. This also mitigates information loss in size reduction blocks (e.g., pooling layer 112).

FIG. 6B illustrates a block diagram of a disclosed CWN 602 integrated within a ResNET-15 CNN architecture.

The CWN 602 comprises a ResNET-15 CNN architecture having five CNN segments 106a-106e and a WN 114 downstream of the five CNN segments 106a-106e. In total, the ResNET-15 CNN architecture comprises 10 convolution blocks 108a-108j, 10 batch normalization blocks 604a-604j, 1 pooling layer 112, and 6 wavelet networks, including additional wavelet networks (WNs) $110_{wn1}$-$110_{wn5}$ and WN 114. The additional WNs $110_{wn1}$-$110_{wn5}$ are implemented as rectification layers within the five CNN segments 106a-106e, while WN 114 is disposed downstream of the five CNN segments 106a-106e as a final activation layer within the CWN 602. In some embodiments, each of the wavelet networks, including additional WNs $110_{wn1}$-$110_{wn5}$ and WN 114 may comprise internal skip connections (e.g., as shown in FIG. 3B) to enable residual learning.

Figure 7:
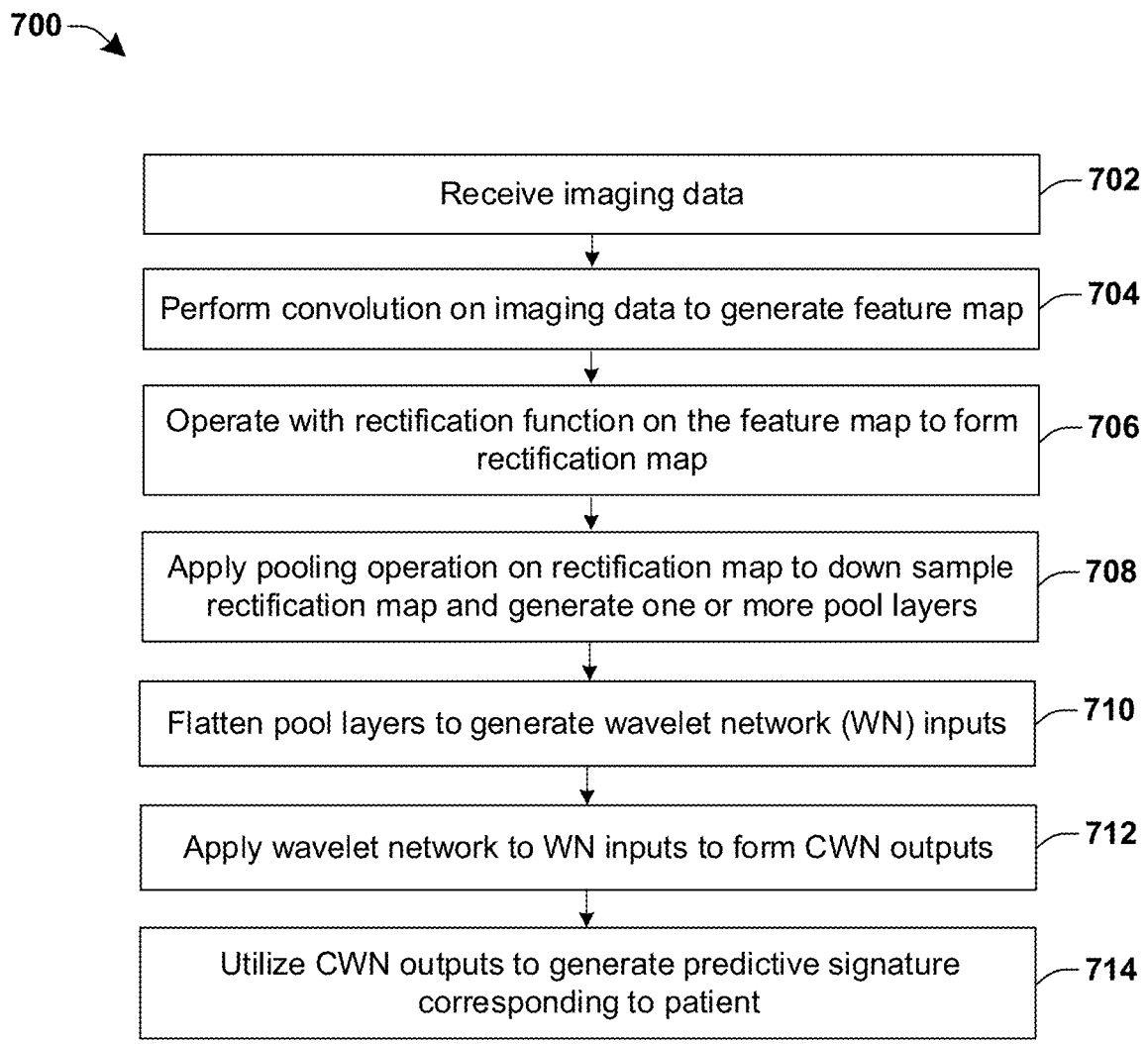
FIG. 7 illustrates a method of performing image analysis using a disclosed CWN having one or more WNs integrated with a CNN architecture.

FIG. 7 illustrates a flow diagram showing some embodiments a method 700 of performing image analysis using a disclosed CWN.

While the disclosed methods (e.g., methods 700, 900, and 1500) are illustrated and described herein as a series of acts or events, it will be appreciated that the illustrated ordering of such acts or events are not to be interpreted in a limiting sense. For example, some acts may occur in different orders and/or concurrently with other acts or events apart from those illustrated and/or described herein. In addition, not all illustrated acts may be required to implement one or more aspects or embodiments of the description herein. Further, one or more of the acts depicted herein may be carried out in one or more separate acts and/or phases.

At act 702, imaging data is received. In some embodiments, the imaging data may comprise one or more digitized radiological images of a bowel of a patient having a bowel disease (e.g., colorectal cancer, rectal cancer, Crohn's disease, and/or the like). The imaging data may comprise one or more radiological images having a plurality of pixels or voxels, with each pixel or voxel having an associated intensity. In some embodiments, the imaging data may comprise a matrix of values that respectively correspond to an intensity of a pixel or voxel within an image.

At act 704, a convolution is performed on the imaging data to form a feature map.

At act 706, a rectification function is operated upon the feature map to generate a rectification map.

At act 708, a pooling operation is performed on the rectification map to down sample the rectification map and generate one or more pooled layers.

At act 710, the pooled layers are flattened to generate wavelet network (WN) inputs.

At act 712, a wavelet network is applied to the WN inputs to generate CWN outputs. The CWN outputs may be indicative of a classification of the imaging data.

At act 714, the CWN outputs may be used to generate a predictive signature corresponding to a patient, in some embodiments. The predictive signature may be associated with a disease response (e.g., to chemotherapy), a disease risk (e.g., a risk of recurrence, overall survival, etc.), or the like.

While the disclosed CWN may be applied to a variety of images in various embodiments, it has been appreciated that the advantages of the disclosed CWN may make the disclosed CWN highly impactful for identifying predictive signatures of a treatment response via medical images (e.g., radiological images such as MRI images, MRE images, CT images, or the like). This is because the disclosed CWN is capable of identifying subtle image features (e.g., orientation and shift differences in an image) that may be important in making medical diagnoses. Such subtle orientation and shift differences could be used to distinguish between a responsive tumor and a non-responsive tumor, in some embodiments.

For example, rectal cancer is a disease in which cancer cells develop in the rectum (e.g., about the last 12 centimeters of the large intestine). Over 40,000 rectal cancer patients are diagnosed annually in the United States alone. A significant clinical problem is identifying those who will or will not respond to standard-of-care chemoradiation treatment. While clinical assessments of pre-treatment MRI has not been significantly associated with pathologic complete response (pCR), the disclosed CWN may be able to learn features associated with pCR on pre-treatment MRI and thereby suggest a more accurate prediction of a response to chemoradiation treatment in rectal cancers. This approach could bring together complementary aspects of radiomics (capturing specific texture patterns from imaging) and deep learning (intelligently learning signatures from imaging data directly) into a single framework, thus offering improved model performance and interpretability for disease characterization.

Figure 8:
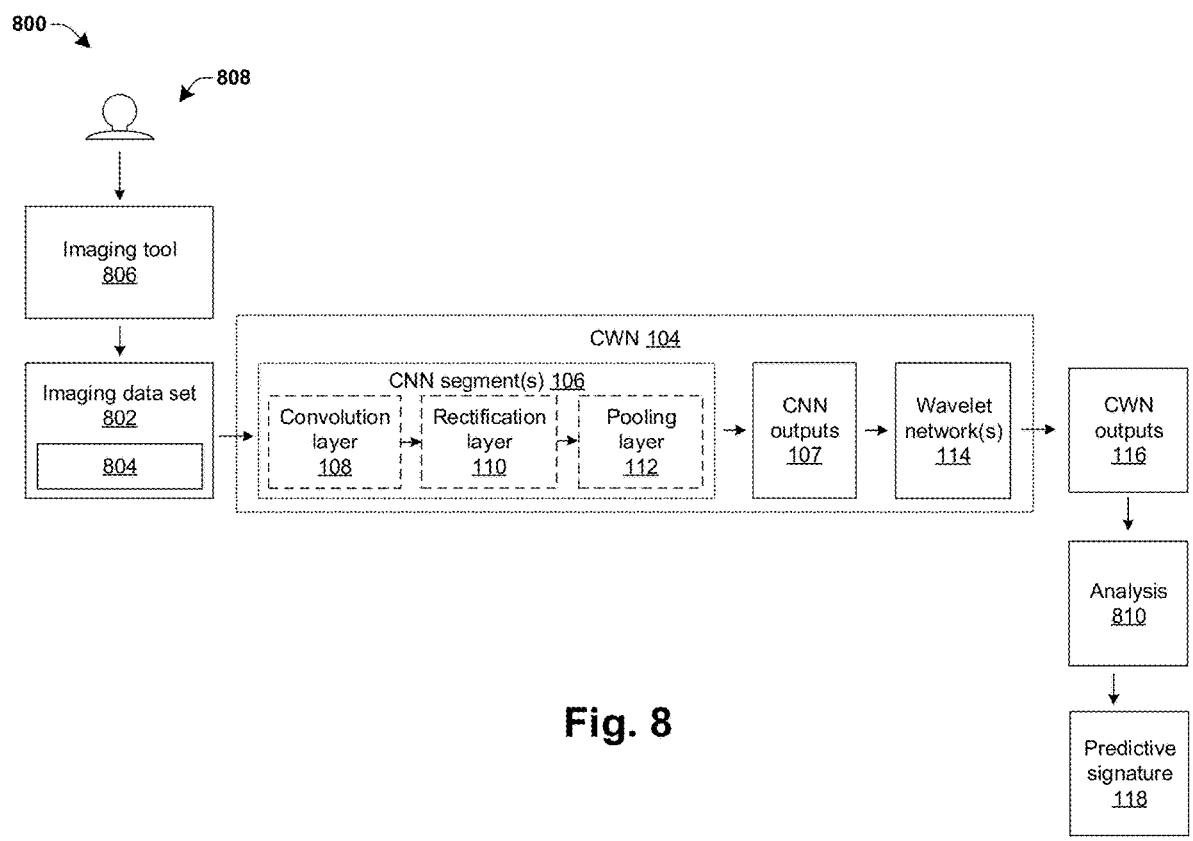
FIG. 8 illustrates a block diagram showing some embodiments of a medical image analysis system comprising a disclosed CWN.

FIG. 8 illustrates a block diagram showing some embodiments of a medical image analysis system 800 comprising a disclosed CWN.

The medical image analysis system 800 comprises an imaging dataset 802 including imaging data from one or more radiological images 804. In some embodiments, the imaging dataset 802 may be formed by operating a radiological imaging tool 806 upon a patient 808 to generate the one or more radiological images 804 of the patient 808. In some embodiments, the one or more radiological images 804 may comprise images of a bowel (e.g., a colon, a rectum, etc.) of the patient 808. In some embodiments, the patient 808 may have rectal cancer, such that the one or more radiological images 804 comprise lesions (e.g., tumors). In other embodiments, the patient 808 may have Crohn's disease, such that the one or more radiological images 804 comprise strictures.

In various embodiments, the one or more radiological images 804 may comprise two-dimensional (2D) images including a plurality of pixels respectively having an intensity or three-dimensional (3D) images including a plurality of voxels respectively having an intensity. In some embodiments, the one or more radiological images 804 may comprise a volume of images including a stack of 2D images that collective form a 3D image. The one or more radiological images 804 may be comprised within an imaging dataset 802. In additional embodiments, a part of the one or more radiological images 804 within the imaging dataset 802 may be obtained from an on-line data base.

In some embodiments, the radiological imaging tool 806 may comprise a magnetic resonance imaging (MRI) scanner configured to generate one or more radiological images 804 comprising MRI images. In other embodiments, the radiological imaging tool 806 may comprise a computed tomography (CT) scanner configured to generate one or more radiological images 804 comprising CT images, a magnetic resonance enterography (MRE) scanner configured to generate one or more radiological images 804 comprising MRE images, a computed tomography enterography (CTE) scanner configured to generate one or more radiological images 804 comprising CTE images, or the like. In some embodiments, contrast materials may be administered to the patient 808 (e.g., orally and/or intravenously) prior to imaging by the radiological imaging tool 806.

A CWN 104 is configured to operate upon the one or more radiological images 804 within the imaging dataset 802. The CWN 104 comprises one or more CNN segments 106 and one or more WNs 114 disposed downstream of the one or more CNN segments 106. The one or more CNN segments 106 are configured to operate upon the one or more radiological images 804 to generate one or more CNN outputs 107. The one or more CNN outputs 107 are provided from one of the one or more CNN segments 106 to one of the one or more WNs 114. The one or more WNs 114 are configured to decompose the one or more CNN outputs 107 according to a mother wavelet to generate one or more CWN outputs 116. In some embodiments, an analysis tool 810 is configured to perform analysis of the one or more CWN outputs 116 to generate a predictive signature 118 of the patient 808 (e.g., a pCR or a non-pCR). The predictive signature 118 may be provided to a health care provider (e.g., by being displayed on a computer screen) and used by the health care provider to generate a prognosis and/or treatment plan to treat the patient 808.

Figure 9:
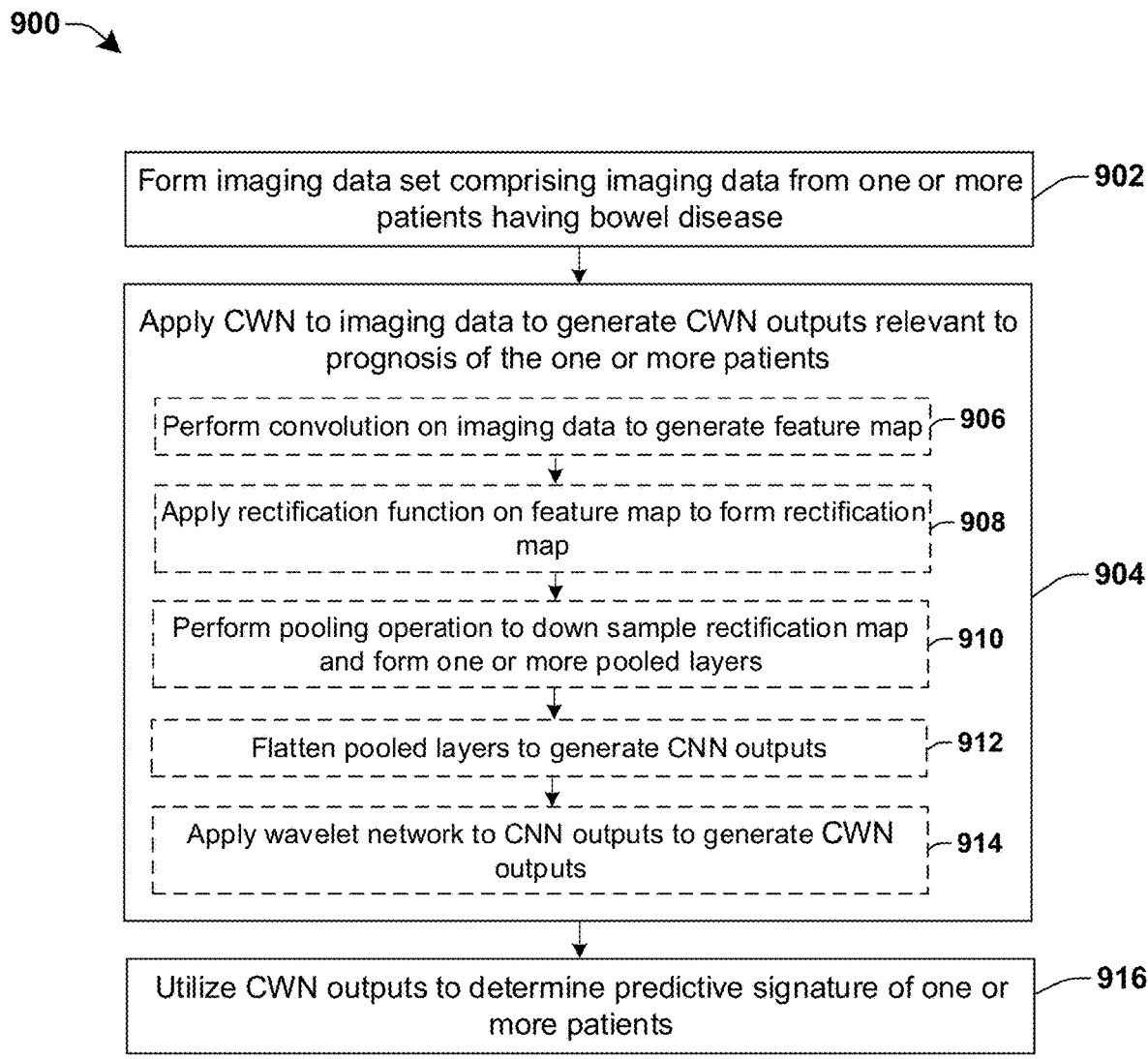
FIG. 9 illustrates a flow diagram showing a method of performing analysis of a radiological image using a disclosed CWN.

FIG. 9 illustrates a flow diagram showing a method 900 of performing medical analysis of a radiological image using a disclosed CWN.

At act 902, an imaging dataset is formed to comprise imaging data from one or more patients having a bowel disease. In some embodiments, the one or more patients may be receiving and/or are to receive treatment (e.g., chemotherapy) for cancer (e.g., rectal cancer). The imaging dataset comprises one or more radiological images generated from radiological scans (e.g., x-rays, CT scans, MRI scans, positron emission tomography (PET) scans, or the like) from of the patient. In some embodiments, the one or more radiological images may include one or more tumors and/or strictures within a rectum of a patient. In some embodiments, the one or more radiological images may comprise pre-treatment images.

At act 904, a CWN is applied to the imaging data to generate a plurality of CWN outputs that are relevant to a prognosis (e.g., a response to treatment) of the one or more patients. The CWN comprises one or more CNN segments and one or more WNs downstream of the one or more CNN segments. In some embodiments, act 904 may be performed according to acts 906-914.

At act 906, a convolution is performed on the imaging data to form a feature map.

At act 908, a rectification function is applied to the feature map to form a rectification map.

At act 910, a pooling operation is performed to downsample the rectification map and to generate one or more pooled layers.

At act 912, the one or more pooled layers are flattened to generate a plurality of CNN outputs.

At act 914, a wavelet network is applied to the plurality of CNN outputs to generate a plurality of CWN outputs.

At act 916, the CWN outputs are used to determine a predictive signature for the one or more patients. In some embodiments, the CWN outputs may be indicative of certain structural or pathological features that may be relevant to a predictive signature. For example, the CWN outputs may be used to exploit subtle differences in oriented and scaled textures between tumors which do and do not respond to chemotherapy. In some embodiments, the subtle differences may be driven by underlying pathologic phenotypes. In some embodiments, the predictive signature corresponds to one or more pathological features such as residual disease, scar tissue, fibrosis, inflammation occurring as a result of disease response, or the like.

Figures 10, 11:
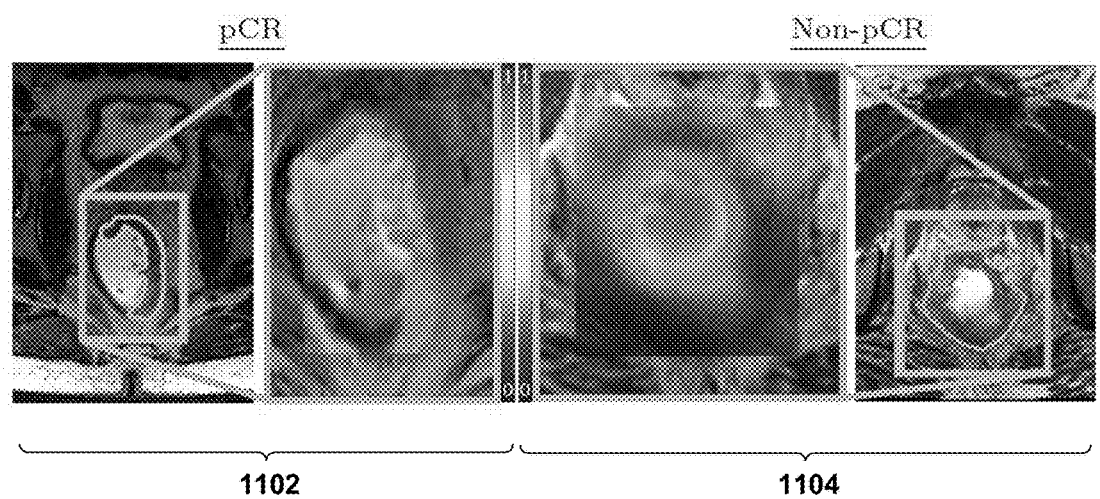
FIG. 10 illustrates a table showing example performance parameters of a disclosed DHCWN in comparison to different machine learning models operated for distinguishing a pathologic complete response (pCR) from a non-pCR.
FIG. 11 illustrates exemplary images showing Grad-CAM heatmaps overlaid on pCR tumor ROI and non-pCR tumor ROI.

FIG. 10 illustrates a table 1000 showing example performance parameters of a disclosed DHCWN in comparison to different machine learning models operated for distinguishing a pathologic complete response (pCR) from a non-pCR.

Table 1000 summarizes patient-wise classification performance for a pathologic complete response (pCR) vs. a non-pCR for a disclosed deep hybrid convolutional wavelet network (DHCWN) in comparison to a conventional convolutional neural network (CNN) and a multilayer wavelet perceptron (DWN-MLP). The disclosed DHCWN yielded the best overall performance in both training sets and hold-out validation sets, which was found to be significantly higher than alternative approaches. For example, the image-wise accuracy of the training sets for the CNN was 69.04%, for the DWN-MLP was 64.83%, and for the DHCWN was 90.67%. Furthermore, the image-wise accuracy of the hold-out validation sets for the CNN was 71.56%, for the DWN-MLP was 76.33%, and for the DHCWN was 91.17%. The patient-wise performance measures were based on aggregating the predicted classes across all 2D images sections within each patient.

Furthermore, the DHCWN was found to be more computationally efficient than the DWN-MLP. For example, the DWN-MLP had a run-time of 398.37 minutes, while the DHCWN had a run-time of 112.59 minutes. The run-time of the DHCWN was marginally worse than the run-time of the CNN.

FIG. 11 illustrates exemplary images 1100 showing Gradient-weighted Class Activation Mapping (Grad-CAM) heatmaps overlaid on pCR tumor ROI and non-pCR tumor ROI. Grad-CAM is a class-discriminative technique that forms a coarse localization map of important regions on an image based on class-specific gradient information flowing into a final convolution layer of a CNN. The Grad-CAM heatmaps enable interpretation of differences in network performance.

The exemplary images 1100 comprise representative Grad-CAM heatmaps of pCR patients 1102 and non-pCR patients 1104. Within the Grad-CAM maps, warmer colors (e.g., red, yellow, etc.) indicate stronger network responses and primary locations of interest for a network. As red regions correspond to high scores in the Grad-CAM visualization, a tumor region of interest appears to be the location of primary focus by a DHCWN in pCR patients 1102. By comparison, the network appears to localize the lumen-wall boundary in non-pCR patients 1104, which may be related to known tumor growth differences between response groups. Therefore, the exemplary images 1100 illustrate that the disclosed DHCWN is able to consistently identify relevant locations within a region of interest for pCR classification.

In some embodiments, a Grad-CAM heatmap corresponding to CWN outputs of a disclosed CWN may be compared to a pathology image (e.g., an MRI pathology) to determine a correlation between the CWN outputs and pathological features (e.g., anatomic features of the pathology image). Because the CWN outputs are able to capture complicated patterns within a digitized image, the CWN outputs may be able to achieve a highly accurate correlation between re relevant locations within a region of interest and the pathological features. The highly accurate correlation can allow for the disclosed CWN to identify pathological features (e.g., residual disease, scar tissue, fibrosis, inflammation occurring as a result of disease response, etc.) that contribute to a predictive signature of a disease. In some embodiments, the identification of such pathological features can be used to further improve the predictive signature.

FIGS. 12A-12B illustrate tables, 1200 and 1212, showing example performance parameters of disclosed DHCWNs having different Mother wavelets in comparison to different machine learning models operated to distinguish a pCR from a non-pCR. In some embodiments, the different machine learning models were trained over 350 epochs, with a batch size of 64, a learning rate of 0.0001, a cross-entropy loss function, and the Adam optimization function (weight decay=0.0001).

FIG. 12A shows a table 1200 that summarizes patient-wise classification performance for 2D machine learning models operated to distinguish pCR from non-pCR.

Table 1200 illustrates performance parameters for a CNN 1202, for a DWN-MLP 1204 having a mother wavelet comprising a Mexican hat, for a DWN-MLP 1206 having a mother wavelet comprising a Morlet function, for a disclosed DHCWN 1208 having a mother wavelet comprising a Mexican hat, and for a disclosed DHCWN 1210 having a mother wavelet comprising a Morlet function. For each of the different machine learning models, table 1200 shows a runtime (measured in minutes), accuracies for discovery sets (e.g., training sets) and hold-out validation sets (e.g., testing sets), and AUCs (area-under curve) for the discovery sets and the hold-out validation sets.

Table 1200 illustrates that the disclosed DHCWN 1208 and disclosed DHCWN 1210 provide for a significant improvement of both accuracy and AUC over the CNN 1202, the DWN-MLP 1204, and the DWN-MLP 1206. In some embodiments, the improvement may be in a range of between approximately 20% and approximately 30% for both the accuracy and the AUC. Furthermore, the disclosed DHCWN 1208 and disclosed DHCWN 1210 provide for a significantly higher computational efficiency (e.g., a lower run-time) than the DWN-MLP 1204 and DWN-MLP 1206 and a computational efficiency (e.g., runtime) that is marginally lower than the CNN 1202.

Table 1200 also shows that the DHCWN 1210 using a mother wavelet comprising a Morlet function provides for improved accuracy and AUC in comparison to the DHCWN 1208 using a mother wavelet comprising a Mexican hat function. This suggests the disclosed DHCWN architecture may be able to exploit more complex texture patterns by changing a mother wavelet.

FIG. 12B shows a table 1212 that summarizes patient-wise classification performance for 3D machine learning models operated to distinguish pCR from non-pCR.

Table 1212 illustrates performance parameters for a regular CNN 1214, for a DWN-MLP 1216 having a mother wavelet comprising a Mexican hat, for a DWN-MLP 1218 having a mother wavelet comprising a Morlet function, for a disclosed DHCWN 1220 having a mother wavelet comprising a Mexican hat, and for a disclosed DHCWN 1222 having a mother wavelet comprising a Morlet function. For each of the different machine learning models, table 1212 shows a runtime, accuracies for discovery sets (e.g., training sets) and hold-out validation sets, and AUCs for the discovery sets and the hold-out validation sets.

Table 1212 illustrates that the disclosed DHCWN 1220 and the disclosed DHCWN 1222 provide for a significant improvement of both accuracy and AUC over the CNN 1214, the DWN-MLP 1216, and the DWN-MLP 1218. In some embodiments, the improvement may be in a range of between approximately 20% and approximately 30% for both the accuracy and the AUC. Furthermore, the disclosed DHCWN 1220 and the disclosed DHCWN 1222 provide for a significantly higher computational efficiency (than DWN-MLP 1216 and DWN-MLP 1218 and a computational efficiency that is marginally lower than the CNN 1214. In some embodiments, Pairwise Wilcoxon testing with multiple comparison correction may be used to assess significant differences in accuracies and AUCs between DHCWN and each of the CNN and the DWN-MLP.

Figure 13A:
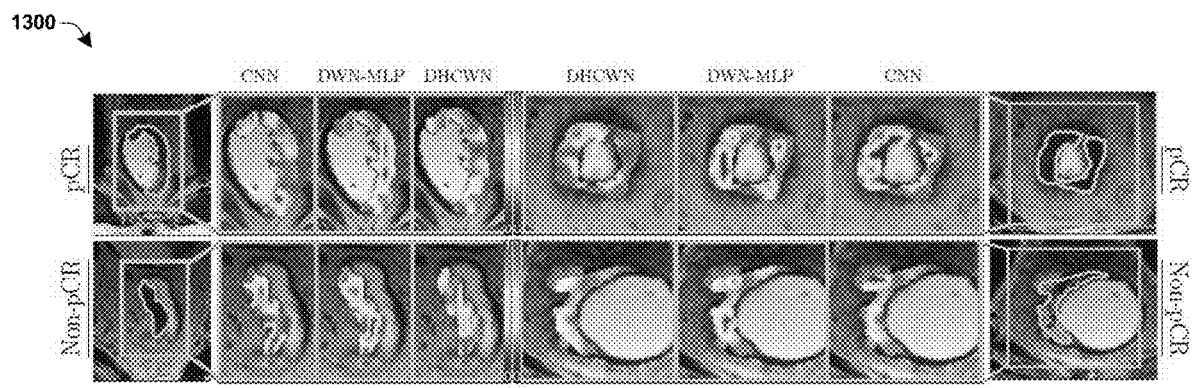
FIG. 13A illustrates exemplary images showing Grad-CAM heatmaps overlaid on pCR tumor ROI and non-pCR tumor ROI.

FIG. 13A illustrates exemplary images 1300 showing Grad-CAM heatmaps overlaid on pCR tumor ROI and non-pCR tumor ROI.

The exemplary images 1300 illustrate representative Grad-CAM visualizations for 2D models comparing heatmaps between DHCWN, CNN, and DWN-MLP networks. The representative Grad-CAM heatmaps are overlaid on pCR tumor ROI (top row) and non-pCR tumor ROI (bottom row). Warmer colors (e.g., red, yellow) indicate stronger network responses and primary locations of attention for the network. The wavelet function within DHCWN was the Morlet function As red regions correspond to high scores in the Grad-CAM visualization, the tumor ROI appears to be the location of primary focus by the DHCWN in pCR patients. By comparison, CNN and DWN exhibit more blue regions in their heatmap suggesting misclassification patterns and poorer performance of these networks in identifying pCR patients (e.g., patients that experience pCR) and non-pCR patients (e.g., patients that experience non-pCR). Non-pCR patients show different trends in blue regions for CNN and DWN-MLP, further indicating these networks paid less attention to certain portions of the tumor. The DHCWN appears to have paid more consistent attention to every part of the annotated tumor across both pCR and non-pCR patients (e.g., having minimal blue and almost uniform red throughout).

Figure 13B:
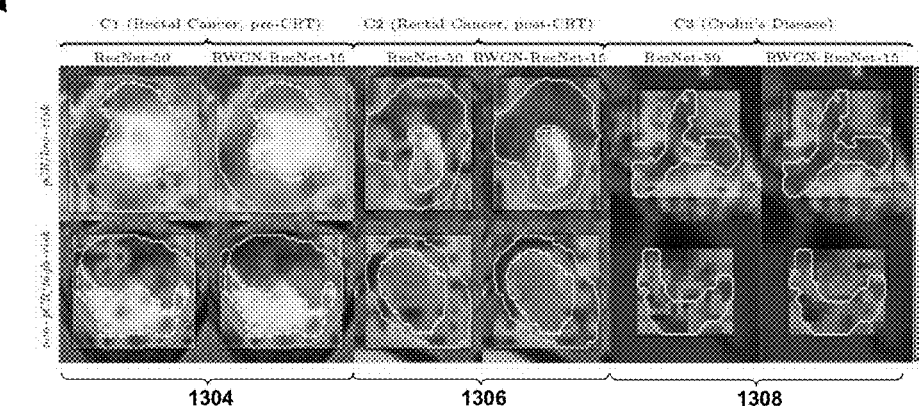
FIG. 13B illustrates exemplary images showing Kernel Shapley Additive exPlanation (SNAP) maps overlaid on pCR tumor ROI and non-pCR tumor ROI.

FIG. 13B illustrates exemplary images 1302 showing SHAP maps overlaid on MR images for a disclosed RWCN (RWCN-ResNet-15) and a CNN model (ResNet-50). The exemplary images 1302 show pCR (e.g., low-risk) patients in the top-row and non-pCR (e.g., high-risk) patients in the bottom row. Images 1304 correspond to pre-treatment images of a patient having rectal cancer prior to neoadjuvant chemoradiation (nCRT). Images 1306 correspond to post-treatment images of a patient having rectal cancer after nCRT. Images 1308 correspond to images of a patient having Crohn's disease. In images 1304, regions outlined in green are a tumor, regions outlined in yellow are a lumen, and regions outlined in pink a rectal wall. In images 1306, regions outlined in green are a tumor and regions outlined in yellow are a lumen. In images 1308, regions outlined in green are a terminal ileum.

The RWCN (RWCN-ResNet-15) appears to have correctly and more homogeneously assigned target class relevance to annotated input regions in non-pCR patients (e.g., more deep red shading within green outlines in the bottom row) in comparison to pCR patients (e.g., top row shows more consistent blue shading within green outlines). Further, the ResNet-50 assigned mixed importance to annotated regions (e.g., lighter shading and mixture of red and blue within all outlines), suggesting lower model confidence as well as suboptimal learning of class-specific responses.

FIG. 14 illustrates a table 1400 showing exemplary performance parameters for disclosed RWCNs in comparison to different machine learning models architectures in distinguishing pCR from non-pCR for different diseases.

Table 1400 summarizes classification accuracy in both discovery sets (e.g., training sets) and hold-out validation sets (e.g., testing sets) for a RWCN-VGG-6 architecture 1402 (e.g., as shown in FIG. 5A) without skip connections, for a RWCN-VGG-6 architecture 1404 (e.g., as shown in FIG. 5A) with skip connections, for a RWCN-ResNet-15 architecture 1406 (e.g., as shown in FIG. 5B) without skip connections, for a RWCN-ResNet-15 architecture 1408 (e.g., as shown in FIG. 5B) with skip connections, for a VGG-16 architecture 1410, for a VGG-16 architecture 1412, for a ResNet-18 architecture 1414, and for a ResNet 50 architecture 1416.

As shown in table 1400, the RWCN-ResNet-15 1406 with identity skip connections was found to yield significantly higher model performance in both discovery sets and hold-out validation sets compared to any alternative RWCN based model as well as all of VGG-16, VGG-19, ResNet-18, and ResNet-50. Furthermore, the VGG-16 architecture, the VGG-16 architecture, the ResNet-18 architecture, and the ResNet 50 architecture are seen to perform equivalently to each other, suggesting that any improvements in performance may be a result of adapting them to incorporate WNs with skip connections. Further, RWCNs using WNs without skip connections (vp=0) perform significantly worse than CNN-based strategies, suggesting the importance of residual learning in these tasks. Notably, all RWCN models exhibit markedly lower runtimes and faster convergence than any CNN model, in addition to using significantly fewer parameters than ResNet and VGG architectures.

Figure 15:
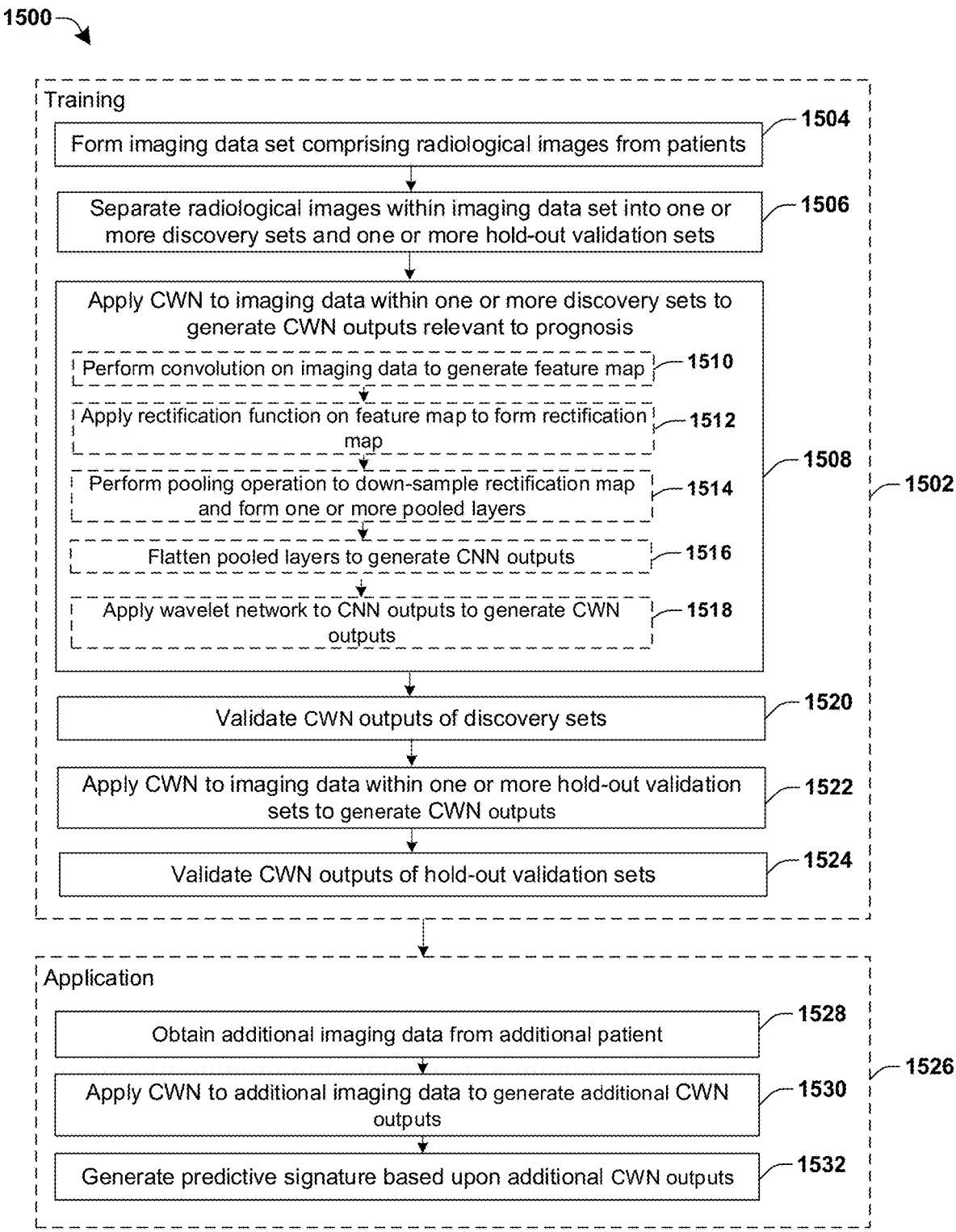
FIG. 15 illustrates a flow diagram of some additional embodiments of a method of generating and applying a disclosed CWN to a patient.

FIG. 15 illustrates a flow diagram of some additional embodiments of a method 1500 of generating and applying a disclosed CWN to a patient.

The method 1500 comprises a training phase 1502 and an application phase 1526. The training phase 1502 is configured to a train a CWN to generate a plurality of CWN outputs that are indicative of a prognosis (e.g., of a pCR response or a non-pCR response). In some embodiments, the training phase 1502 may be performed according to acts 1504-1524.

At act 1504, an imaging dataset is provided and/or formed to comprise a plurality of radiological images. In various embodiments, the plurality of radiological images may comprise pre-treatment images from patients having a bowel disease (e.g., rectal cancer and/or Crohn's disease). In some embodiments, the plurality of radiological images may be obtained from different institutions (e.g., different hospitals, clinics, universities, etc.). In some embodiments, the imaging dataset may comprise more than 100 radiological images, more than 150 radiological images, more than 200 radiological images, etc. In some embodiments, the imaging dataset may comprise 153 pre-treatment rectal cancer MRI scans. In some embodiments, the imaging data may comprise T2 weighted (T2w) MRI scans.

In some embodiments, each of the plurality of radiological images has a corresponding ground truth. In some embodiments, histopathologic tumor regression grade (TRG) assessment of an excised surgical specimen (obtained as per standard-of-care in rectal cancer treatment) was used as the ground truth for pathologic tumor response to nCRT where TRG0 (0% viable tumor cells remaining) was considered as pCR while TRG1-3 were labeled non-pCR.

In some embodiments, the plurality of radiological images may be subjected to one or more quality enhancement operations. For example, in some embodiments the one or more quality enhancement operations may comprise subjecting the plurality of radiological images (e.g., MRI scans) to resampling to ensure a consistent voxel resolution across the cohort (trilinear, 1×1×1 mm). In some embodiments, the one or more quality enhancement operations may comprise using available radiologist annotations of an entire tumor ROI to estimate bounding boxes to span a lesion after connected component analysis to omit ROIs smaller than 20 pixels. Based on the average size of tumor ROIs across the cohort, tumor bounding boxes may be resized (e.g., to 62×62 and 62×62×62 pixels in 2D and 3D, respectively).

At act 1506, the plurality of radiological images within the imaging dataset are separated into one or more discovery sets (e.g., training sets) and one or more hold-out validation sets (e.g., testing sets). In some embodiments, the plurality of radiological images be separated in a manner that causes approximately 70% of radiological images to be placed within the one or more discovery sets and 30% of the radiological images to be placed within the one or more hold-out validation sets.

At act 1508, a CWN is operated upon imaging data within one or more discovery sets to generate a plurality of CWN outputs for the discovery sets. The plurality of CWN outputs are indicative of a prognosis (e.g., of a pCR response or a non-pCR response). In some embodiments, the CWN is configured to operate upon the imaging data according to acts 1510-1518.

At act 1510, a convolution may be performed on the imaging data within the one or more discovery sets to generate a feature map. The convolution may be performed by applying a kernel to the imaging data.

At act 1512, a rectification function is applied to the feature map to form a rectification map.

At act 1514, a pooling operation is performed to down-sample the rectification map and to form one or more pooled layers.

At act 1516, the one or more pooled layers are flattened to generate a plurality of CNN outputs.

At act 1518, a wavelet network is applied to the plurality of CNN outputs to generate a plurality of CWN outputs.

At act 1520, the plurality of CWN outputs from the discovery sets are validated. In some embodiments, the plurality of CWN outputs from the discovery sets may be validated by comparing the plurality of CNN outputs to a corresponding ground truth.

At act 1522, the CWN is operated upon imaging data within one or more hold-out validation sets to generate a plurality of CWN outputs for the hold-out validation sets. In some embodiments, the CWN is configured to operate upon the imaging data within the hold-out validation sets according to acts 1510-1518.

At act 1524, the plurality of CWN outputs from the hold-out validation sets are validated. In some embodiments, the plurality of CWN outputs from the hold-out validation sets may be validated by comparing an output of the CWN to a corresponding ground truth.

The application phase 1526 is configured to utilize the CWN that was trained in the training phase 1502 on one or more additional radiological images, which are taken from an additional patient suspected of having a bowel disease (e.g., rectal cancer and/or Chron's disease). In some embodiments, the application phase 1526 may be performed according to acts 1528-1530.

At act 1528, an additional imaging data is obtained from an additional patient. The additional imaging data may comprise an additional radiological image that is a pre-treatment image of the patient.

At act 1530, the additional imaging data is operated upon by the CWN to generate one or more additional CWN outputs.

At act 1532, a predictive signature is determined from the one or more additional CWN outputs.

Figure 16:
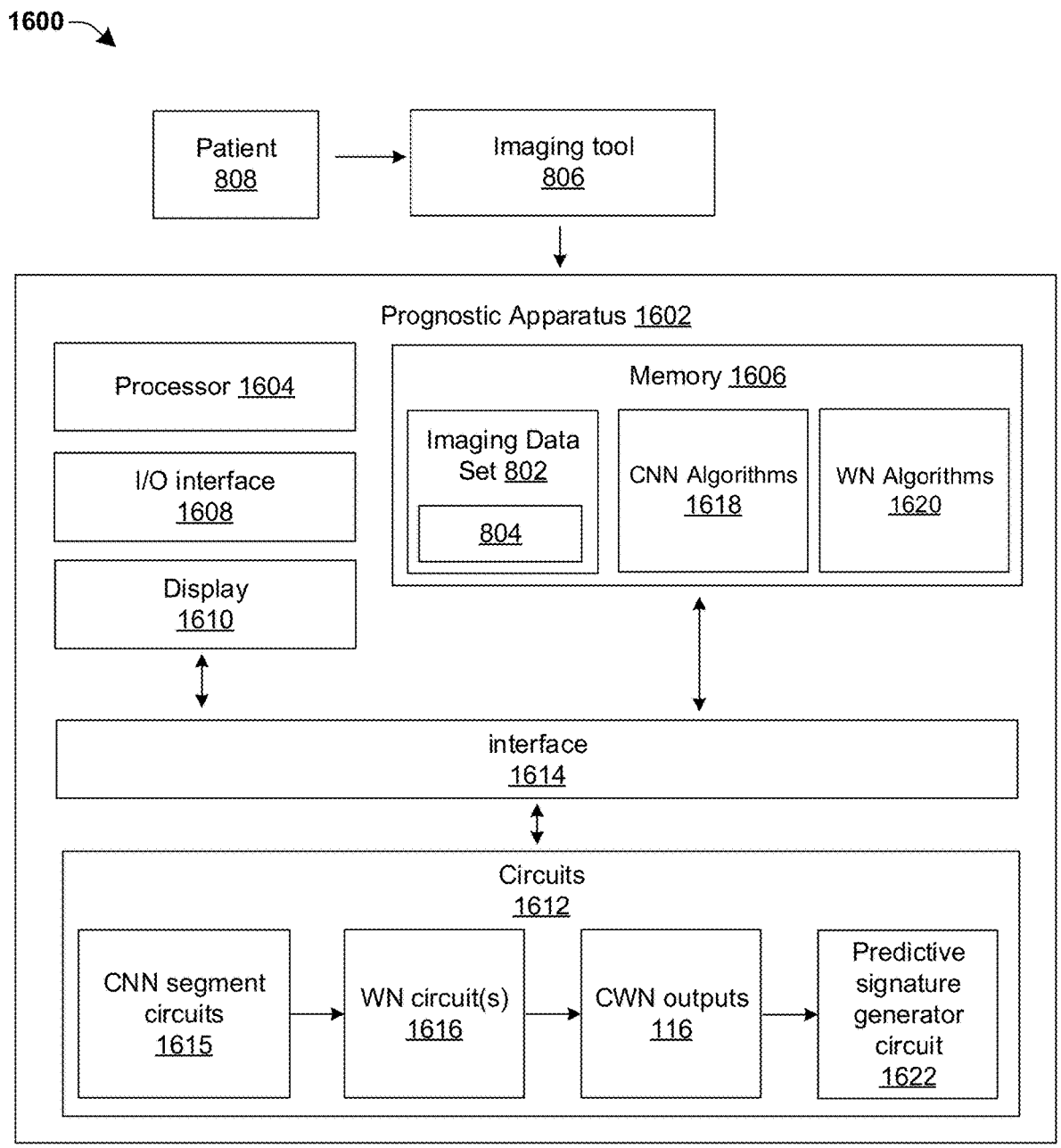
FIG. 16 illustrates a block diagram of some embodiments of an apparatus comprising a CWN that is configured to determine a prognosis for a patient.

FIG. 16 illustrates a block diagram of some embodiments of an apparatus 1600 comprising a CWN that is configured to determine a prognosis for a patient.

The apparatus 1600 is configured to generate a prognosis for a patient based upon one or more pre-treatment radiological images. In some embodiments, the apparatus 1600 may be coupled to a radiological imaging tool 806 configured to act upon a patient 808 having or suspected to have rectal cancer and/or Crohn's disease. In various embodiments, the radiological imaging tool 806 may comprise an MRI scanner, an MRE scanner, a CT scanner, a CTE scanner, or the like.

The apparatus 1600 comprises a processor 1604 and a memory 1606. The processor 1604 can, in various embodiments, comprise circuitry such as, but not limited to, one or more single-core or multi-core processors. The processor 1604 can include any combination of general-purpose processors and dedicated processors (e.g., graphics processors, application processors, etc.). The processor(s) 1604 can be coupled with and/or can comprise memory (e.g., memory 1606) or storage and can be configured to execute instructions stored in the memory 1606 or storage to enable various apparatus, applications, or operating systems to perform operations and/or methods discussed herein.

Memory 1606 can be configured to store an imaging dataset 802 comprising one or more radiological images 804 (e.g., CTE images, MRE images, etc.) from one or more patients. Each of the one or more radiological images can have a plurality of pixels or voxels, each pixel or voxel having an associated intensity. In some embodiments, memory 1606 can store one or more radiological images as one or more discovery set(s) for training a disclosed CWN and/or one or more hold-out validation sets for validating the disclosed CWN.

The analysis apparatus 1602 also comprises an input/output (I/O) interface 1608 (e.g., associated with one or more I/O devices), a display 1610, a set of circuits 1612, and an interface 1614 that connects the processor 1604, the memory 1606, the I/O interface 1608, the display 1610, and the set of circuits 1612. The I/O interface 1608 can be configured to transfer data between the memory 1606, the processor 1604, the set of circuits 1612, and external devices, for example, a medical imaging device such as a CTE scanner, an MRE scanner, or the like.

The set of circuits 1612 can comprise one or more CNN segment circuits 1615 and one or more wavelet network circuits 1616. In some embodiments, the set of circuits 1612 may comprise hardware components. The set of circuits 1612 are configured to access the imaging dataset 802. The one or more CNN segment circuits 1615 are configured to operate upon the one or more radiological images 804 with CNN algorithms 1618 stored in the memory 1606 to generate a plurality of CNN outputs. The one or more wavelet network circuits 1616 are configured to operate upon the plurality of CNN outputs with one or more WN algorithms 1620 to generate CWN outputs 116. In some additional embodiments, the set of circuits 1612 may further comprise a predictive signature generator circuit 1622. The predictive signature generator circuit 1622 is configured to generate a predictive signature relating to a disease of a patient.

Therefore, the present disclosure relates to a convolutional wavelet network (CWN) that utilizes both deep learning (e.g., convolutional neural networks) and wavelet networks to generate a prognosis from a digitized image of a patient.

In some embodiments, the present disclosure relates to a non-transitory computer-readable medium storing computer-executable instructions that, when executed, cause a processor to perform operations, including forming an imaging dataset having imaging data corresponding to one or more radiological images of a patient with a bowel disease; operating upon the imaging data with one or more convolutional neural network (CNN) segments configured to generate a plurality of CNN outputs, the one or more CNN segments respectively having a convolution layer configured to perform a convolution on the imaging data; applying a wavelet network to the plurality of CNN outputs to generate a plurality of convolution wavelet network (CWN) outputs, the wavelet network being configured to decompose the plurality of CNN outputs according to a mother wavelet; and constructing a predictive signature associated with disease response or risk based on the plurality of CWN outputs.

In other embodiments, the present disclosure relates to a method of image analysis, including forming an imaging dataset having imaging data corresponding to one or more pre-treatment radiological images of a patient with a bowel disease; performing a convolution on the imaging data to form a feature map; performing a rectification function on the feature map to form a rectification map; performing a pooling operation on the rectification map to form a plurality of CNN outputs; applying a wavelet network to the plurality of CNN outputs, the wavelet network being configured to decompose the plurality of CNN outputs into a plurality of different versions of a mother wavelet respectively having different wavelet shift parameters and wavelet scale parameters, and to generate a plurality of CWN outputs from the plurality of different versions of the mother wavelet; and constructing a predictive signature for the patient based on the plurality of CWN outputs, the predictive signature being associated with disease response or risk.

In other embodiments, the present disclosure relates to an image analysis system, including a memory configured to store an imaging dataset having imaging data corresponding to one or more pre-treatment radiological images of a patient having a bowel disease; one or more convolutional neural network (CNN) segments configured to perform one or more convolutions on the imaging data to generate a plurality of CNN outputs; a wavelet network disposed downstream of the one or more CNN segments, the wavelet network being configured to decompose the plurality of CNN outputs into a plurality of wavelons and to generate a plurality of CWN outputs by summing differently weighted versions of the plurality of wavelons, the plurality of wavelons respectively including different versions of a mother wavelet that has been shifted and scaled according to different wavelet shift parameters and different wavelet scale parameters; and a predictive signature generator configured to generate a predictive signature relating to the bowel disease of the patient.

Examples herein can include subject matter such as an apparatus, a digital whole slide scanner, a CT system, an MRI system, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system, according to embodiments and examples described.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable medium storing computer-executable instructions that, when executed, cause a processor to perform operations, comprising:
    forming an imaging dataset comprising imaging data corresponding to one or more radiological images of a patient having a bowel disease;
    operating upon the imaging data with one or more convolutional neural network (CNN) segments configured to generate a plurality of CNN outputs, wherein the one or more CNN segments respectively comprise a convolution layer configured to perform a convolution on the imaging data;
    applying a wavelet network to the plurality of CNN outputs to generate a plurality of convolution wavelet network (CWN) outputs, wherein the wavelet network is configured to decompose the plurality of CNN outputs according to a mother wavelet; and
    constructing a predictive signature associated with disease response or risk based on the plurality of CWN outputs.

2. The non-transitory computer-readable medium of claim 1, wherein operating upon the imaging data with the one or more CNN segments comprises:
    performing the convolution on the imaging data to form a feature map;
    operating upon the feature map with a rectification function to form one or more rectification maps;
    performing a pooling operation on the one or more rectification maps to form a plurality of pooled layers; and
    flattening the plurality of pooled layers to form the plurality of CNN outputs.

3. The non-transitory computer-readable medium of claim 2, wherein the wavelet network comprises four or more hidden layers.

4. The non-transitory computer-readable medium of claim 2, wherein the rectification function is an additional wavelet network.

5. The non-transitory computer-readable medium of claim 1, wherein the wavelet network comprises:
    an input layer configured to receive the plurality of CNN outputs;
    a hidden layer comprising a plurality of wavelons respectively having different versions of the mother wavelet; and
    an output layer comprising the plurality of CWN outputs, the plurality of CWN outputs being a function of a sum of different wavelon weight parameters of the plurality of wavelons.

6. The non-transitory computer-readable medium of claim 5, wherein the different versions of the mother wavelet within the plurality of wavelons are formed by applying different wavelet shift parameters and different wavelet scale parameters to the mother wavelet.

7. The non-transitory computer-readable medium of claim 5, wherein the plurality of CWN outputs are a function of a wavelon bias parameter added to the sum of the different wavelon weight parameters of the plurality of wavelons.

8. The non-transitory computer-readable medium of claim 5, wherein the wavelet network comprises one or more skip connections extending between the input layer and the output layer, the plurality of CWN outputs being a function of weighted versions of the one or more skip connections.

9. The non-transitory computer readable medium of claim 1, wherein the predictive signature corresponds to one or more of residual disease, scar tissue, fibrosis, and inflammation occurring as a result of disease response.

10. The non-transitory computer-readable medium of claim 1, further comprising:
    utilizing the plurality of CWN outputs to determine if a tumor will have a pathologic complete response (pCR) or a non-pCR to chemotherapy.

11. The non-transitory computer-readable medium of claim 1, wherein the plurality of CWN outputs are a function of a wavelet shift parameter, a wavelet scale parameter, a wavelon bias parameter, and a wavelon weight parameter.

12. A method of image analysis, comprising:
   forming an imaging dataset comprising imaging data corresponding to one or more pre-treatment radiological images of a patient having a bowel disease;
   performing a convolution on the imaging data to form a feature map;
   performing a rectification function on the feature map to form a rectification map;
   performing a pooling operation on the rectification map to form a plurality of CNN outputs;
   applying a wavelet network to the plurality of CNN outputs, wherein the wavelet network is configured to decompose the plurality of CNN outputs into a plurality of different versions of a mother wavelet respectively having different wavelet shift parameters and wavelet scale parameters, and to generate a plurality of CWN outputs from the plurality of different versions of the mother wavelet; and
   constructing a predictive signature for the patient based on the plurality of CWN outputs, the predictive signature being associated with disease response or risk.

13. The method of claim 12, wherein the plurality of CWN outputs are a function of wavelon bias parameters added to a sum of products of different wavelon weight parameters and the plurality of different versions of the mother wavelet.

14. The method of claim 12, wherein the wavelet network comprises one or more skip connections extending between an input layer comprising the plurality of CNN outputs and an output layer comprising the plurality of CWN outputs, the plurality of CWN outputs being a function of weighted versions of the one or more skip connections.

15. The method of claim 12, wherein the rectification function is an additional wavelet network.

16. The method of claim 12, further comprising:
   utilizing the plurality of CWN outputs to determine a treatment plan for the patient comprising pharmaceutical therapy or surgery.

17. An image analysis system, comprising:
   a memory configured to store an imaging dataset comprising imaging data corresponding to one or more pre-treatment radiological images of a patient having a bowel disease;
   one or more convolutional neural network (CNN) segments configured to perform one or more convolutions on the imaging data to generate a plurality of CNN outputs;
   a wavelet network disposed downstream of the one or more CNN segments, the wavelet network being configured to decompose the plurality of CNN outputs into a plurality of wavelons and to generate a plurality of CWN outputs by summing differently weighted versions of the plurality of wavelons, wherein the plurality of wavelons respectively comprise different versions of a mother wavelet that has been shifted and scaled according to different wavelet shift parameters and different wavelet scale parameters; and
   a predictive signature generator configured to generate a predictive signature relating to the bowel disease of the patient.

18. The image analysis system of claim 17, wherein the wavelet network comprises:
   an input layer configured to receive the plurality of CNN outputs;
   a hidden layer comprising the plurality of wavelons; and
   an output layer comprising the plurality of CWN outputs.

19. The image analysis system of claim 18, wherein the wavelet network comprises one or more skip connections extending between the input layer and the output layer, the plurality of CWN outputs being a function of weighted versions of the one or more skip connections.

20. The non-transitory computer readable medium of claim 17, wherein the predictive signature corresponds to one or more of residual disease, scar tissue, fibrosis, and inflammation occurring as a result of disease response.

* * * * *